(12) United States Patent
Eardley et al.

(10) Patent No.: US 10,682,466 B2
(45) Date of Patent: Jun. 16, 2020

(54) DRUG INJECTION DEVICE WITH CARTRIDGE HOLDER AUTOMATICALLY OPERATING CLUTCH ALLOWING RESET OF DRIVE MECHANISM AND DRIVE SPRING RE-LOADING UPON CARTRIDGE EXCHANGE

(71) Applicant: Sanofi, Paris (FR)

(72) Inventors: Zoë Georgina Eardley, Warwickshire (GB); Paul Richard Draper, Evesham Worcestershire (GB)

(73) Assignee: Sanofi, Paris (FR)

( * ) Notice: Subject to any disclaimer, the term of this patent is extended or adjusted under 35 U.S.C. 154(b) by 418 days.

(21) Appl. No.: 15/533,917

(22) PCT Filed: Dec. 9, 2015

(86) PCT No.: PCT/EP2015/079168
§ 371 (c)(1),
(2) Date: Jun. 7, 2017

(87) PCT Pub. No.: WO2016/091978
PCT Pub. Date: Jun. 16, 2016

(65) Prior Publication Data
US 2017/0326303 A1  Nov. 16, 2017

(30) Foreign Application Priority Data

Dec. 10, 2014  (EP) ..................................... 14306996

(51) Int. Cl.
*A61M 5/315* (2006.01)
*A61M 5/20* (2006.01)
(Continued)

(52) U.S. Cl.
CPC ........... *A61M 5/31543* (2013.01); *A61M 5/20* (2013.01); *A61M 5/24* (2013.01); *A61M 5/3157* (2013.01);
(Continued)

(58) Field of Classification Search
CPC .......... A61M 5/178; A61M 2005/2006; A61M 2005/2485; A61M 2005/3125;
(Continued)

(56) References Cited

U.S. PATENT DOCUMENTS

2011/0077595 A1   3/2011  Eich et al.

FOREIGN PATENT DOCUMENTS

EP      2301611        3/2011
EP      2301611  A1 *  3/2011   .......... A61M 5/1452
(Continued)

OTHER PUBLICATIONS

International Preliminary Report on Patentability in International Application No. PCT/EP2015/079168, dated Jun. 13, 2017, 8 pages.
(Continued)

*Primary Examiner* — Jason E Flick
(74) *Attorney, Agent, or Firm* — Fish & Richardson P.C.

(57) ABSTRACT

The present disclosure relates to an injection device for setting and dispensing of a dose of a medicament, the device comprising:
  an elongated main housing to accommodate a cartridge filled with the medicament and defining an axial direction,
  a piston rod arranged inside the main housing and extending in axial direction along a first axis to operably engage with a piston of the cartridge,
  a reset member axially displaceable inside the main housing between a proximal operating position and a distal reset position along a second axis radially offset
(Continued)

from the first axis to switch the device between a reset mode and an operating mode, a cartridge holder releasably attachable to a distal end of the main housing on the first axis to accommodate a distal end of the cartridge, wherein the cartridge holder comprises a sidewall portion with a radially outwardly protruding lock member to axially engage with the reset member located radially adjacent the cartridge holder.

19 Claims, 9 Drawing Sheets

(51) Int. Cl.
 A61M 5/24 (2006.01)
 A61M 5/31 (2006.01)
(52) U.S. Cl.
 CPC ..... *A61M 5/31541* (2013.01); *A61M 5/31553* (2013.01); *A61M 5/31585* (2013.01); *A61M 5/31593* (2013.01); *A61M 2005/202* (2013.01); *A61M 2005/2481* (2013.01); *A61M 2005/2488* (2013.01); *A61M 2005/3126* (2013.01); *A61M 2205/581* (2013.01); *A61M 2205/582* (2013.01); *A61M 2205/583* (2013.01); *A61M 2205/586* (2013.01)
(58) Field of Classification Search
 CPC .......... A61M 2205/58; A61M 5/31533; A61M 5/31535; A61M 5/31545; A61M 5/31548; A61M 5/31565; A61M 5/31583; A61M 5/3159; A61M 2005/202; A61M 2005/2481; A61M 2005/2488; A61M 2005/3126; A61M 2205/581; A61M 2205/582; A61M 2205/583; A61M 2205/586; A61M 5/20; A61M 5/24; A61M 5/31541; A61M 5/31543; A61M 5/31553; A61M 5/3157; A61M 5/31585; A61M 5/31593
 USPC ........................................................ 604/186
 See application file for complete search history.

(56) References Cited

FOREIGN PATENT DOCUMENTS

| EP | 2626095 | 8/2013 |
| WO | WO 2010/139632 | 12/2010 |
| WO | WO 2010/139637 | 12/2010 |
| WO | WO 2011/039207 | 4/2011 |

OTHER PUBLICATIONS

International Search Report and Written Opinion in International Application No. PCT/EP2015/079168, dated Feb. 11, 2016, 7 pages.

* cited by examiner

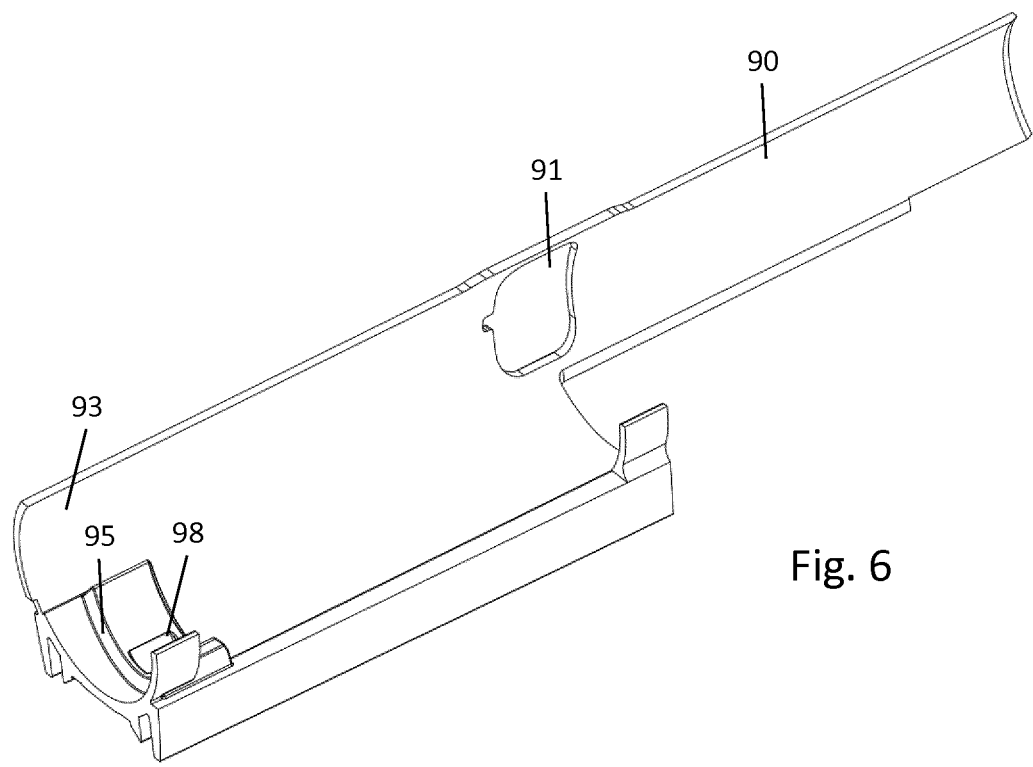
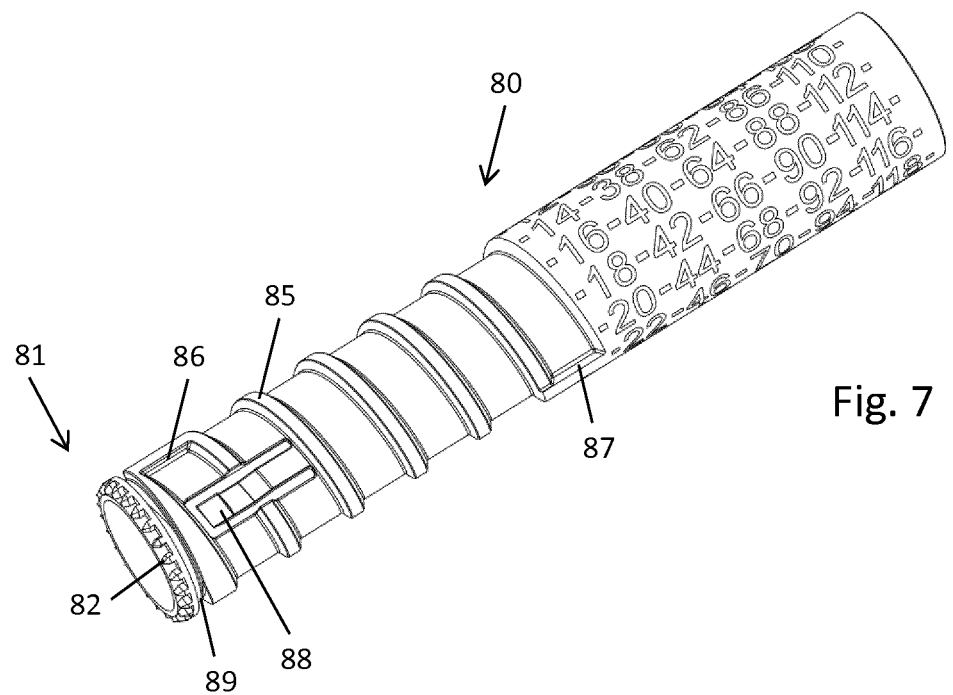

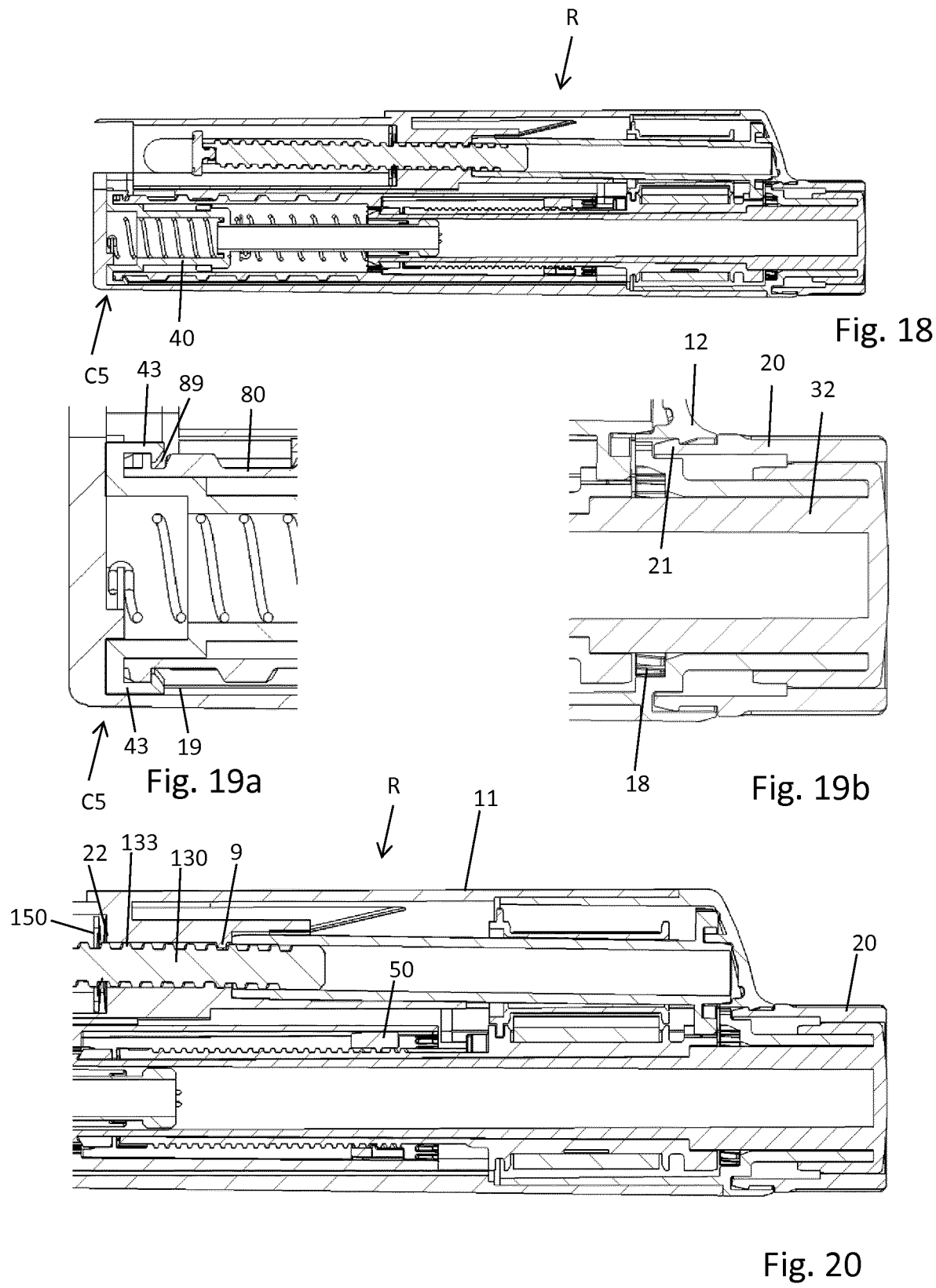

DRUG INJECTION DEVICE WITH CARTRIDGE HOLDER AUTOMATICALLY OPERATING CLUTCH ALLOWING RESET OF DRIVE MECHANISM AND DRIVE SPRING RE-LOADING UPON CARTRIDGE EXCHANGE

CROSS-REFERENCE TO RELATED APPLICATIONS

This application is a U.S. national stage application under 35 USC § 371 of International Application No. PCT/EP2015/079168, filed on Dec. 9, 2015, which claims priority to European Patent Application No. 14306996.1, filed on Dec. 10, 2014, the entire contents of which are incorporated herein by reference.

TECHNICAL FIELD

The present disclosure relates to a drive mechanism of a drug delivery device and to a drive mechanism of an injection device, such like an injection pen. In particular the disclosure relates to a resettable drive mechanism of a reusable injection device that allows and enables a user of the device to reset the drive mechanism when an empty cartridge of the device is to be replaced by a new one.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be entirely discarded when the medicament in the cartridge has been completely dispensed or used-up.

Reusable devices typically comprise an access opening to remove an empty cartridge and to insert a filled or new cartridge into the device instead. Some injection devices comprise a multi-component housing, e.g. a proximally-located body that is releasably engaged with a distal cartridge holder. While the body accommodates and contains the mechanical components of a drive mechanism the cartridge holder at least partially accommodates the replaceable cartridge and keeps the cartridge in a well-defined position in regard to the drive mechanism, in particular in regard to the piston rod. A distal end of the cartridge holder or of the housing of the injection device is releasably connectable with a piercing assembly, typically comprising a double-tipped injection needle that is configured and designed to pierce a distal seal of the cartridge in order to obtain access to the interior thereof for expelling of a well-defined amount of the medicament from the cartridge through the distally-directed advancing motion of the piston rod.

Many injection devices, of e.g. pen-injector type, provide multiple and frequent dispensing and injection of the liquid medicament. For this, the piston rod of the drive mechanisms of such devices advances in discrete steps in a distal direction during repeated dose dispensing procedures until an end-of-content configuration has been reached, in which the piston of the cartridge reaches a distal stop or end configuration. Since the piston rod of the drive mechanism has been correspondingly and successively displaced in distal direction also the piston rod is located in a distal end-of-content position when an empty cartridge is to be replaced by a new or filled one.

For reusable injection devices it is therefore required that the drive mechanism provides a reset mechanism or reset function by way of which at least the piston rod is displaceable into an initial configuration, i.e. a zero dose configuration or zero dose position.

SUMMARY

In certain aspects, a reset mechanism for an injection device applicable to set and to dispense a dose of a medicament is provided. In certain aspects, a reusable injection device including such a reset mechanism is provided. In certain aspects, a reset mechanism for an injection device having a mechanical energy storage, which energy storage is chargeable with mechanical energy during a reset operation, is provided. In particular, a reset mechanism for an injection device equipped with a pre-loaded spring serving as energy storage for providing a driving force or driving torque to a drive mechanism of the injection device and hence to induce a distally directed advancing motion of a piston rod in order to expel a predefined amount of the medicament from a cartridge is provided. In certain aspects, a rather simple and user friendly handling of the injection device not only for dose setting and dose dispensing but also for resetting of the injection device, in particular of its drive mechanism, is provided. The reset mechanism can be implementable only with a minimum number of additional components. Furthermore, the reset mechanism can be rather compact and space saving.

In a first aspect an injection device for setting and dispensing of at least a single, preferably of multiple doses of a medicament, typically a liquid medicament includes an elongated main housing to at least partially accommodate a cartridge filled with the medicament. The main housing defines an axial direction. The main housing comprises a distal end facing towards biological tissue and an oppositely located proximal end face facing away from biological tissue, into which the medicament is to be injected.

The injection device comprises a drive mechanism consisting of numerous mechanically interacting or inter-engaging components that are rotatable and/or axially displaceable in order to set a dose of variable size and for subsequently dispensing the dose of the medicament. The injection device further comprises a piston rod arranged inside the main housing and extending in axial direction along a first axis to operably engage with a piston of the cartridge. The piston of the cartridge seals the tubular barrel of the cartridge in proximal direction. The piston rod is adapted to advance in distal direction so as to exert distally directed pressure to the piston of the cartridge. In this way, a fluid pressure inside the cartridge can be increased to expel a predefined amount of the medicament from the cartridge, which for the purpose of dose dispensing is typically connected with a piercing assembly having a double-tipped injection needle.

The injection device further comprises a reset member axially displaceable inside the main housing between a proximal operating position (O) and a distal reset position (R). The reset member is arranged on or along a second axis. The second axis is located radially offset from the first axis. Typically, first and second axes extend substantially parallel but are arranged radially next to each other, hence at a certain radial distance from each. Components of the drive mechanism that are concentrically arranged along the first axis are radially offset in a non-overlapping position with regard to components being arranged concentrically along the second axis.

The reset member is displaceable inside the main housing in axial direction between the proximal operating position and the distal reset position in order to switch the device between a reset mode and an operating mode. In the operating mode the injection device is switchable between a dose setting mode and a dose dispensing mode. In dose setting mode a dose of variable size can be set whereas in dose dispensing mode the previously set dose is dispensable from the cartridge.

The injection device further comprises a cartridge holder that is releasably attachable to a distal end of the main housing. The cartridge holder is arranged on or along the first axis and serves to accommodate at least a distal end of the cartridge. The cartridge holder further comprises a sidewall portion featuring a radially outwardly protruding lock member with a cam portion. The lock member with its cam portion is adapted and configured to axially engage with the reset member that is located radially adjacent to the cartridge holder.

Cartridge holder and reset member are concentrically arranged along first and second longitudinal axes that are separated from each other by a predefined radial distance. Only the lock member radially outwardly extending from a sidewall portion of the cartridge holder partially overlaps in radial direction with the reset member. It is due to the radially outwardly protruding cam portion of the cartridge holder that the cartridge holder may axially engage with the reset member in order to allow or to induce an axial displacement of the reset member in the course of cartridge holder detachment or cartridge holder attachment, respectively.

The lock member not only supports or induces axial displacement of the reset member but also provides or at least supports axial fixing of the cartridge holder to the main housing. In this way, the lock member fulfils a double function. It provides a fixing means for the cartridge holder to releasably attach and to releasably fix the cartridge holder to the main housing and it further provides and induces axial displacement of the reset member, typically in proximal direction to shift the reset member in the proximal operating position upon fixing of the cartridge holder to the main housing. In particular, the lock member axially fixes the cartridge holder to the main housing.

The reset member is typically axially slidably engaged with the main housing but is rotationally locked to the main housing. In other words, the reset member and the main housing are mutually engaged by a splined interface. In this way, the reset member is only allowed to be axially displaced inside the main housing but is prevented from rotating with respect to the main housing with regard to the second axis.

The cartridge holder might be connectable and releasable to and from the main housing through a twisting motion. In particular, the cartridge holder and main housing may be mutually connected through a bayonet type coupling. Also here the lock member may serve to provide a bayonet member engaging with the correspondingly shaped bayonet member of the main housing. It is also conceivable, that the cartridge holder is attachable and fixable to the main housing through a purely twisting motion without an axial displacement. Mutual fixing of cartridge holder and main housing would then not influence the axial position of the cartridge accommodated by mutually interconnected cartridge holder and main housing.

According to an embodiment the reset member is displaceable in distal direction and into the reset position under the action of at least one spring element. Accordingly, the reset member is displaceable relative to the main housing in proximal direction along the second axis into the operating position against the action of at least one spring element. By means of the at least one spring element the reset member is automatically displaceable in distal direction as soon as the cartridge holder is disconnected from the main housing. Disconnection of the cartridge holder therefore automatically switches the injection device into the reset mode. The cam portion of the cartridge holder typically blocks such a distally directed displacement of the reset member. As soon as the cartridge holder is for instance unlocked with regard to the main housing, e.g. by means of a twisting motion relative to the main housing, the tangentially displaceable cam portion gives way for the reset member to advance in distal direction to reach the reset position.

In a further embodiment the distal end of the reset member axially abuts with an inside facing portion of a distally located front face of the main housing when reaching the distal reset position. The main housing terminates in distal direction with the distally located front face and therefore provides an axial distal abutment for the reset member. The cartridge holder, typically comprising a cup-shaped or cylindrically-shaped sleeve-like geometry is arranged radially adjacent to the front face of the main housing. The front face of the main housing is arranged in the region of the second axis while the cartridge holder is arranged on or along the first axis radially adjacent thereto. The cartridge holder or at least a distal portion thereof may axially distally protrude from the front face of the main housing when overlapping with the first axis.

According to another embodiment the cam portion of the lock member of the cartridge holder tangentially engages a distal edge of the reset member such that the reset member is displaced in proximal direction towards the operating position when the cartridge holder is twisted relative to the main housing with regard to the first axis and in a tangential locking direction. The cam portion of the cartridge holder axially squeezes between the distal edge of the reset member and the inward facing portion of the front face of the main housing. In this way, the cam portion abuts in distal direction against the inside facing portion of the front face and further engages and abuts in proximal direction with the distally located edge of the reset member. Due to and according to the geometry of the cam portion a twisting of the cartridge holder leads to a continuous proximal displacement of the reset member towards its proximal operating position. The twisting motion of the cartridge holder may be accompanied by an axial displacement of the cartridge holder relative to the main housing. Alternatively, the twisting of the cartridge holder is purely rotationally without any axial displacement relative to the main housing.

The axial abutment between the lock member and the front face of the main housing not only provides axial support for the lock member and its cam portion acting as a wedge entering and increasing an axial gap or slit between reset member and front face. In addition, the lock member and cam portion axially engaging with the front face serves to axially lock the cartridge holder to the main housing. In an axial position substantially overlapping with the lock member the main housing comprises a recessed portion in a sidewall portion adjacent to the distally located front face. The lock member with a distally facing abutment surface may then axially engage with the proximally facing inside portion of the distally located front face of the main housing. In this way the cam portion not only serves to axially displace the reset member but also provides an axial interlock between main housing and cartridge holder.

In another embodiment the lock member is axially sandwiched between the reset member and the inside of the main housing's front face when the reset member is in the operating position. The sidewall portion of the cartridge holder may further comprise a kind of a tangential or circumferential gap or slit distally adjacent to the cam portion. This gap or slit portion of the cartridge holder's sidewall may be configured to receive and to engage with a lateral, hence a radial outer edge of the main housing's front face. The cartridge holder typically comprises a gripping surface distally spaced from the lock member. The gap or slit may then be axially confined in proximal direction by the at least slightly radially protruding gripping surface and in distal direction by the lock member of the cartridge holder. The gripping surface may then axially abut an outward facing portion of the front face of the main housing when the cartridge holder is attached thereto.

According to another embodiment the reset member is axially engaged with a dose indicator that is rotationally supported on the second axis and that has consecutive numbers or symbols showing up in a window of the main housing when the dose indicator is subject to a dose incrementing rotation during dose setting or when the dose indicator is subject to a dose decrementing rotation during dose dispensing. Axial engagement between the dose indicator and the reset member is typically obtained by means of snap features of reset member and dose indicator.

The axial connection of reset member and dose indicator comprises at least one circumferential rim on one of reset member and dose indicator and at least one snap feature of the other one of reset member and dose indicator engaging with said rim. In this way, the dose indicator is free to rotate relative to the reset member but is axially slaved to the reset member. An axial displacement of the reset member between the proximal operating position and the distal reset position therefore equally transfers to the dose indicator. In this way, it is even possible to visualize in the window of the main housing that the injection device is actually in reset mode.

The reset member and the dose indicator are permanently axially engaged. When in proximal operating position the dose indicator is axially fixed through the interaction with the reset member. The dose indicator, typically comprising a tubular sleeve with consecutive numbers or symbols on an outer surface thereof is threadedly engaged with a gauge element. The gauge element is radially sandwiched between the dose indicator and the interior of the main housing. The gauge element is typically rotatably locked to the housing but is free to move in axial direction relative to the housing. Due to its permanent threaded engagement with the dose indicator it travels in axial direction when the dose indicator is subject to rotation relative to the housing.

Typically, the gauge element is non-transparent and opaque to cover most numbers or symbols of the dose indicator that would otherwise show up in the window of the main housing. The gauge element further comprises at least one recess or a window through which at least one number or symbol of the dose indicator is visible.

The dose indicator and the gauge element further comprise mutually corresponding stop elements by way of which a maximum rotation of the dose indicator can be limited, thereby acting as a single dose limiting mechanism. The gauge element and the dose indicator may each comprise two mutually corresponding stop elements in order to limit a dose decrementing rotation of the dose indicator at the end of a dose dispensing procedure. The mutually corresponding stop elements of gauge element and dose indicator therefore provide a zero dose stop and a maximum dose stop for the drive mechanism.

The zero dose stop is operable to prevent dialling of a negative dose as well as to provide a well-defined end of a dispensing process. The maximum dose stop serves to limit the maximum amount of a dose to be set by the device.

According to another embodiment the dose indicator comprises a detent structure at a distal end to engage with a correspondingly-shaped detent structure of the main housing when reaching the reset position. By means of mutually corresponding detent structures of dose indicator and main housing the dose indicator is selectively rotatably lockable with the main housing, in particular when switching the injection device into the reset mode. During a reset procedure or reset operation a rotation of the dose indicator is therefore prevented.

The main housing's detent structure may be located at the inside facing portion of the main housing's front face and the corresponding detent structure of the dose indicator may be located at a distal front face thereof. The distal front face of the dose indicator and a distal front face of the reset member may flush as seen in radial direction. Distal ends of the reset member and the dose indicator may be located also at a slight axial offset provided that the detent structure of the main housing's front face at least slightly protrudes in proximal direction. The mutually engaging detent structures typically comprise mutually engaging axially and proximally extending teeth in order to provide a rotational interlock between main housing and dose indicator when switching the injection device into the reset mode.

According to another embodiment the injection device further comprises a dispensing member aligned along the second axis with a distal shaft portion and further having a proximal button portion. The dispensing member is axially displaceable relative to the main housing in distal direction against the action of a dispensing spring element in order to switch the injection device from a dose setting mode (S) into a dose dispensing mode (D). The button portion serves as a proximally located dose button that is typically depressible in distal direction by the thumb of a user to induce and to control a dispensing action of the injection device.

The dispensing member may be further permanently rotatably engaged with a dose dial located at a proximal end of the housing of the injection device. Hence, the dispensing member is axially slidably supported inside the main housing and may be rotatable for at least setting of a dose. The dispensing member with its distal shaft portion may be selectively rotatably lockable to the dose indicator in order to set a dose of variable size when the device is in dose setting mode. In dose dispensing mode, the dispensing member is rotatably decoupled from the dose indicator so that the dose indicator is enabled to return into a zero dose position without inducing a rotation of the dispensing member.

When in dose dispensing mode the dispensing member and hence the dose dial may be rotatable relative to the main housing. Since the dispensing member is rotatably disengaged from driving components of the drive mechanism during dose dispensing, any rotation of either the dose dial or the dispensing member has no measurable effect on the operation of the injection device.

According to a further embodiment the injection device further comprises a drive sleeve permanently rotationally coupled to the piston rod, rotationally biased by a mainspring, rotationally locked to the main housing in dose setting mode and rotationally released from the main housing in dose dispensing mode. The drive sleeve is exclusively rotatable relative to the main housing during dose dispensing for advancing the piston rod in distal direction. The drive sleeve may be directly or indirectly rotatably coupled to the piston rod so that the piston rod rotates during dose dispensing.

The threaded piston rod may be threadedly engaged with the housing so that the piston rod experiences a distally directed advancing motion upon a rotation induced by the drive sleeve. The mainspring is permanently engaged and coupled to the drive sleeve and is typically pre-tensed to such a degree, that the mechanical energy stored in the mainspring is sufficient to displace the piston rod from an initial proximal position into a final distally located position, in which the entirety of the medicament initially provided in the cartridge has been dispensed.

The mainspring is therefore a preloaded spring, that is rechargeable during a reset operation. The permanent coupling of the drive sleeve with the piston rod and with the mainspring and the selective coupling and rotational locking of drive sleeve and main housing is beneficial in terms of a user friendly handling of the injection device. Typically, the rotational lock between drive sleeve and main housing in dose setting mode allows a user-induced dose setting without acting against the preloaded mainspring. Dose setting is therefore rather easy and does not require biasing of the mainspring. It is only due to a distally directed displacement of the drive sleeve, typically by means of the dispensing member, that the drive sleeve rotationally disengages from the housing and is liberated to rotate under the action of the mainspring.

In the course of a combined distally directed displacement of dispensing member and drive sleeve for dispensing of a dose, the dispensing member is rotationally decoupled from the dose indicator and the drive sleeve is rotationally coupled or rotationally locked to the dose indicator. In this way, the rotating drive sleeve induces a corresponding rotation of the dose indicator in a dose decrementing direction in order to return the dose indicator into an initial configuration.

In another embodiment the injection device further comprises a ratchet member that is permanently axially and permanently rotationally locked to the dispensing member. The ratchet member is typically attached to a distal end of the dispensing member, in particular to a distal end of the dispensing member's shaft portion. The ratchet member provides an audible and/or tactile signal during dose setting, hence when the dispensing member is subject to a dose incrementing or dose decrementing rotation relative to the housing and/or relative to the drive sleeve. Typically, the ratchet member comprises numerous ratchet teeth that engage with correspondingly-shaped ratchet teeth of the drive sleeve, which is rotationally locked to the housing in dose setting mode. During dose setting, the ratchet member and the dispensing member are both subject to rotation relative to the drive sleeve. Due to the ratchet engagement between the ratchet member and the drive sleeve, regular click sounds or respective tactile signals are generated indicating to the user, that a dose is incremented or decremented in discreet steps.

In a further embodiment the ratchet member is alternately in a ratchet engagement with the drive sleeve when in dose setting mode or with the reset member when in a reset mode. In dose setting mode the ratchet member is disengaged from the reset member and in reset mode the ratchet member is disengaged from the drive sleeve. The ratchet engagement between the ratchet member and the reset member in reset mode is of particular benefit in order to prevent a self-actuated de-charging of the mainspring. Moreover, in reset mode the drive sleeve and the dispensing member may rotatably lock so that a rotation of the dose button and hence a rotation of the dispensing member is transferable into a rotation of the drive sleeve in order to charge the mainspring.

The ratchet engagement between the ratchet member permanently rotatably locked to the dispensing member and the reset member permanently rotatably locked to the main housing serves to store the mechanical energy of the mainspring during charging thereof. Moreover, the ratchet engagement between reset member and ratchet member in reset mode provides audible and/or tactile feedback to a user, that the reset mode is in progress and that the mainspring is charged in discreet steps while the piston rod is retracted in proximal direction until it reaches an initial configuration that allows to replace the empty cartridge by a new one.

In another embodiment the ratchet member is rotationally locked to the dose indicator when in dose setting mode. The ratchet member is further rotationally released from the dose indicator when in dose dispensing mode. Switching of the injection device from the dose setting mode into the dose dispensing mode axially displaces the ratchet member relative to the dose indicator, thereby releasing a torque-proof clutch between ratchet member and dose indicator.

The ratchet member is displaceable in distal direction when switching the injection device in dose dispensing mode. This distally directed displacement is obtained through the permanent and axial coupling of ratchet member and dispensing member. Selective rotational interlocking or rotational engagement of ratchet member and dose indicator provides a dose incrementing rotation of the dose indicator during dose setting. A decoupling of ratchet member and dose indicator for dose dispensing and a rotational engagement of dose indicator and drive sleeve during dose dispensing provides a dose decrementing rotation of the dose indicator during dispensing of a dose, thereby returning to a zero dose configuration.

According to another embodiment the reset member axially engages with the ratchet member when approaching the distal reset position, thereby distally displacing the ratchet member into a reset position, in which it is disengaged from the drive sleeve. Switching of the injection device into the reset mode is only supported and possible when the injection device is in dose setting mode. In dose setting mode the ratchet member and the drive sleeve are in ratchet engagement. In addition, the drive sleeve is rotatably locked to the main housing as long as the injection device is in dose setting mode.

In order to reset the drive mechanism it is required to recharge the mainspring and to return the piston rod into its proximal starting position. This is obtainable by rotating the drive sleeve in a dose incrementing direction, i.e. in a direction opposite to a dose decrementing direction, in which the drive sleeve rotates during dose dispensing under the action of the mainspring. It is therefore required to abrogate and to release the rotational interlock between drive sleeve and main housing. By means of an engagement of the reset member and the ratchet member when approaching the distal reset position the ratchet member is displaceable in distal direction, thereby releasing the ratchet engagement between ratchet member and drive sleeve.

In the same way and since the ratchet member is permanently axially engaged with the dispensing member also the dispensing member experiences a distally directed displacement relative to the main housing. When switching into reset mode the dispensing member is dragged in distal direction by means of the ratchet member, axially engaged with the reset member, which in turn is spring biased in distal direction. In this way, the proximal button portion of the dispensing member, which in operation mode and in particular in dose setting mode may slightly protrude in axial proximal direction from the main housing or from the dose dial, is retracted in distal direction into the housing. The dispensing member therefore becomes effectively inoperable when switching the injection device into the reset mode.

However, the dispensing member may still provide a torque-transferring function between the rotatable dose dial and the ratchet member.

According to a further embodiment the dispensing member is in axial abutment with the drive sleeve to displace the drive sleeve into a distal reset position, in which the drive sleeve is rotationally released from the main housing and from the dose indicator. The drive sleeve and the dispensing member comprise mutually corresponding radially extending shoulder portions that allow and support a rotation of the drive sleeve relative to the dispensing member when the injection device is in dose dispensing mode. Typically, the drive sleeve comprises a proximally facing abutment portion axially engaging with a distally facing abutment portion of the dispensing member. Distally displacing the dispensing member relative to the housing therefore advances the drive sleeve accordingly in distal direction, thereby releasing the rotational interlock between the drive sleeve and the main housing.

In reset mode, this axial abutment is also of importance since the axial distal displacement of the reset member transfers into a respective distal displacement of the ratchet member. Since the ratchet member is permanently axially engaged with the dispensing member also the dispensing member is driven in axial distal direction by the distally directed displacement of the reset member. Due to the axial abutment of dispensing member and drive sleeve this distally directed displacement of the dispensing member also transfers to a corresponding distally directed displacement of the drive sleeve, thereby rotationally releasing the drive sleeve from the main housing and therefore enabling a rotation of the drive sleeve in e.g. a direction opposite to the dose decrementing direction of rotation for returning the piston rod into its initial axial proximal position and for re-charging the mainspring.

At the same time or even before the drive sleeve rotatably disengages from the main housing the drive sleeve rotatably engages and rotatably interlocks with the dispensing member. In this way, a torque-proof engagement between dose dial, dispensing member and drive sleeve can be established by way of which the drive sleeve is rotatable in a desired direction when rotating the dose dial at a proximal end of the injection device. Since the ratchet member is in ratchet engagement with the rotationally locked reset member when the injection device is in reset mode the rotation of the drive sleeve against the action of the mainspring for re-charging the same is secured against unintentional or self-actuated discharging of the mainspring.

In a further embodiment the dispensing member axially intersects the hollow drive sleeve. A proximal head of the reset member, which is located inside the dispensing member, further engages with at least one latch member of the dispensing element during a distally directed displacement towards the reset position, thereby activating a torque-proof clutch between the drive sleeve and the dispensing member. In operating mode drive sleeve and dispensing member are axially engaged but are rotationally disengaged. When switching the injection device into the reset mode, a torque-proof rotational interlock between drive sleeve and dispensing member is established. In this way, a manually-induced rotation of a dose dial rotatably coupled or rotatably interlocked with the dispensing member equally transfers into a respective rotation of the drive sleeve, thereby re-charging the mainspring and returning the piston rod into an initial proximal position.

The injection device is particularly implemented as a so called auto-injector, wherein the mainspring serves as a mechanical energy storage, by way of which a driving or dispensing force or torque is provided for the injection of the medicament. The mainspring is typically preloaded to such an extent, that the mechanical energy stored therein is sufficient to expel the entirety of the medicament located inside the cartridge. Between consecutive dispensing actions a biasing or recharging of the mainspring is therefore not required. During dose setting a user does not have to provide a torque against the action of a spring element for eventually biasing the same. It is only during a reset operation that the mainspring or drive spring is recharged and that the piston rod is retracted into its initial proximal position.

In the present context, the distal direction points in the direction of the dispensing end of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29 LysB30 human insulin; B30-N-palmitoyl-ThrB29 LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, a non-limiting embodiment of the injection device with its drive mechanism is described in detail by making reference to the drawings, in which:

FIG. 6 is an isolated view of a main housing portion of the injection device, FIG. 7 is a perspective illustration of the dose indicator, FIG. 18 shows the device after reaching the reset position, FIG. 19a is an enlarged view of a distal end of the device according to FIG. 18, FIG. 19b is an enlarged view of the proximal end of the device according to FIG. 18, FIG. 20 is illustrative of the device according to FIG. 18 during a reset operation.

DETAILED DESCRIPTION

Figure 1:
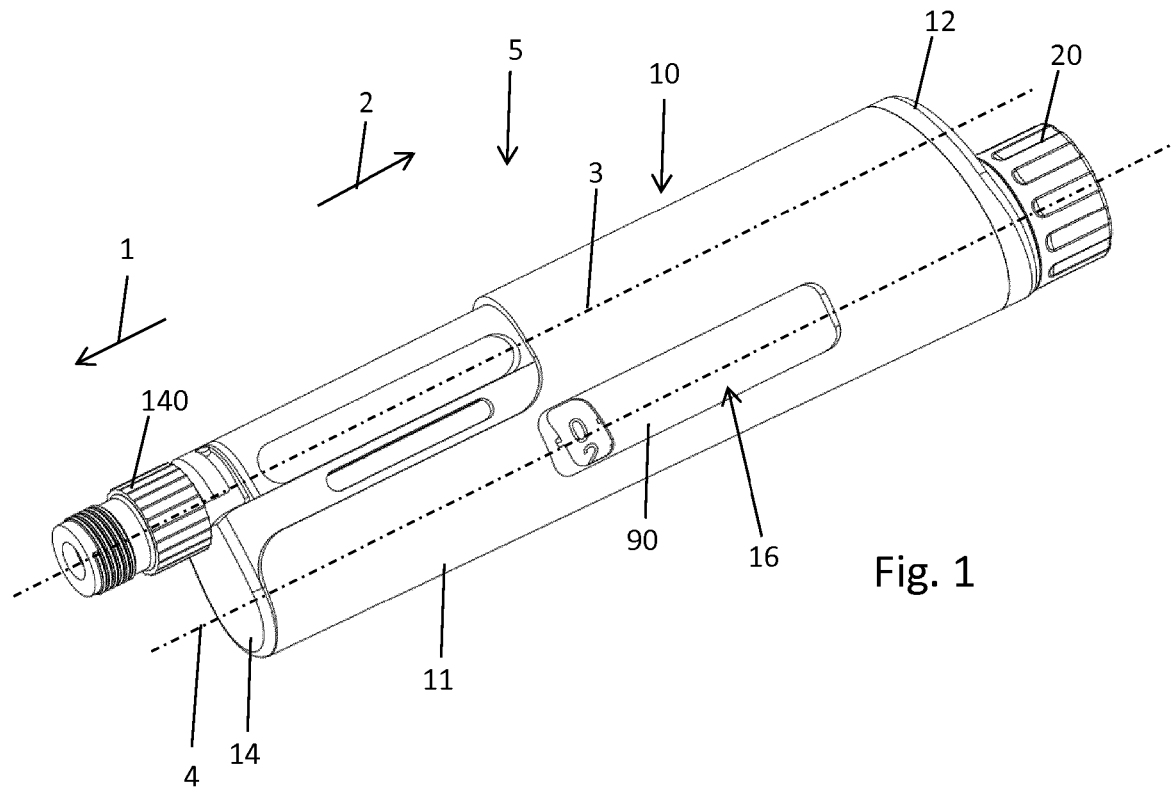
FIG. 1 shows a perspective view of the injection device.
Figure 2:
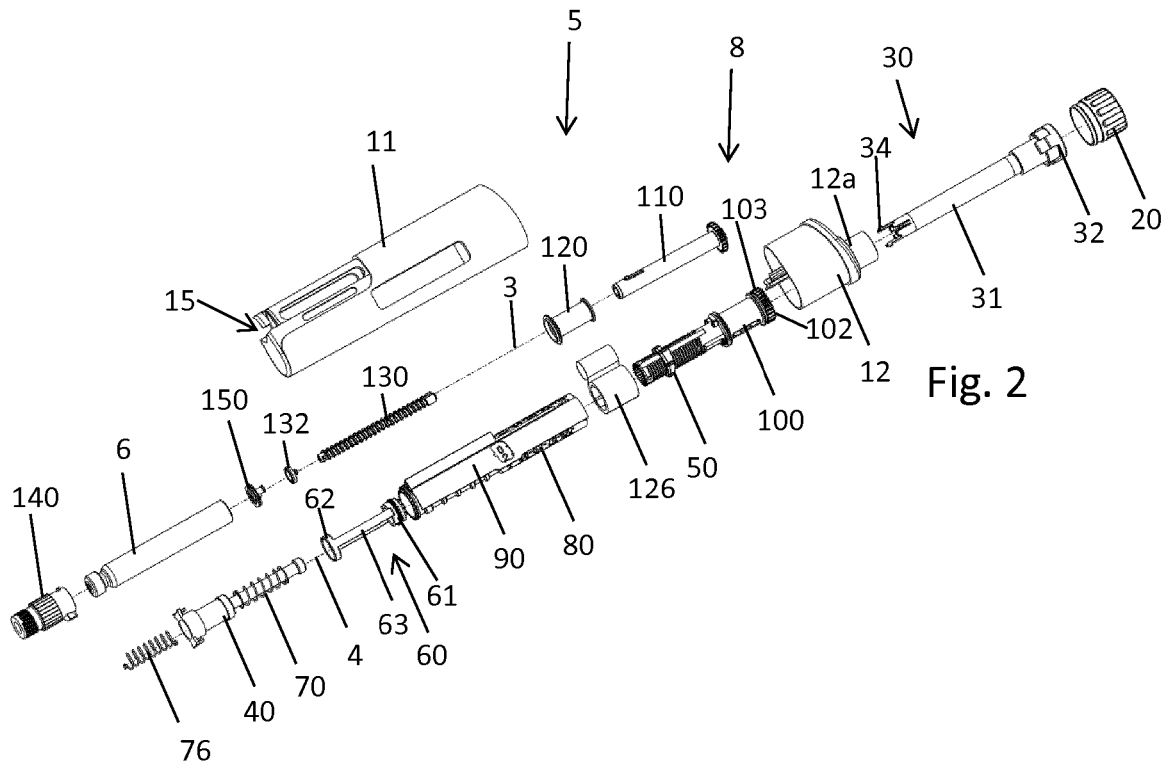
FIG. 2 shows an exploded and perspective view of the various device components.

The injection device 5 as illustrated in FIG. 1 is configured as an all mechanically implemented auto-injector. It comprises a housing 10 featuring a main housing 11 of elongated shape and extending in an axial direction. The main housing 11 comprises a distal end facing in a distal direction 1 and further comprising a proximal end facing in a proximal direction 2. The housing 10 comprises a proximal housing portion 12 that is connectable with a proximal end of the main housing 11. The proximal housing portion 12 serves as a kind of a lid closing the tubular-shaped main housing 11 in proximal direction 2. As shown in FIG. 2, the proximal housing portion 12 comprises a proximally extending socket portion 12a that serves as a support and a bearing for a dose dial 20 being rotatably supported on the housing 10. The dose dial is rotationally supported on the housing portion 12 but is axially fixed thereto by means of at least one clip member 21 as shown in FIG. 19b.

In distal direction 1 the main housing 11 terminates with a distal front face 14 from which a detachable cartridge holder 140 axially protrudes. The cartridge holder 140 comprises a threaded socket 141 to threadedly engage with a piercing assembly, typically comprising a needle hub with a double-tipped injection needle. The cartridge holder comprises a through opening 142 in its distal front face to receive the proximal end of the injection needle. The cartridge holder 140 further comprises an outer gripping surface 143 that allows and supports to releasably attach the cartridge holder 140 to the main housing 11 through a twisting motion with regard to a first axis 3 extending parallel to the longitudinal extension of the main housing 11.

As it becomes further apparent from FIGS. 2-5 there is provided a second axis 4 along which a series of further components of the drive mechanism 8 of the injection device 5 are arranged. Almost all mechanical components of the injection device 5 as they are illustrated in FIG. 2 are located concentrically about one of the two principal axes 3, 4.

Along the first axis 3 there are located the cartridge 6 and the piston rod 130. The piston rod 130 is rotatably engaged with a sleeve-shaped drive member 110 so that a rotation of the drive member 110 axially fixed to the main housing 11 leads to a distally directed displacement of the piston rod 130. This distally advancing displacement may be obtained through a splined interconnection of piston rod 130 and drive member 110 and further by a threaded engagement of the piston rod 130 with a threaded flange portion 9 of the main housing 11. The piston rod 130 extends into the interior of the hollow drive member 110.

In an alternative embodiment it is also conceivable, that the piston rod 130 is in splined engagement with the main housing 11, i.e. the piston rod 130 is free to be axially displaced relative to the main housing 11 but is for instance threadedly engaged with the hollow drive member 110.

The drive member 110 is in permanent rotational engagement with a drive sleeve 100 which is arranged radially adjacent to the drive member 110. As can be seen from FIGS. 2 and 3, the drive member 100 is arranged along the second principal axis 4. Concentrically arranged with this second axis 4 there is further provided the sleeve-shaped dispensing member 30, the dose dial 20, a gauge element 90, the dose indicator 80, the ratchet member 60 as well as the reset member 40.

The dose dial 20 is axially fixed to the housing 10, in particular to the proximal housing portion 12, e.g. by way of mutually engaging latch or clip members 21, e.g. positively locked and positively engaged with a corresponding recess of the proximal housing portion 12. In this way, the dose dial 20 is rotatable relative to the housing 10. The dose dial is permanently rotatably locked to the dispensing member 30 having a proximal button portion 32 at least slightly proximally protruding from the proximal end of the dose dial 20 when in dose setting mode (S).

The dispensing member 30 further has a shaft portion 31 extending along the second axis 4. The dispensing member 30 comprises at least one, typically several radially outwardly biased snap members 34 at its distal end to permanently axially engage with a ratchet member 60. In this way, the dispensing member 30 and the ratchet member 60 are permanently axially and rotatably locked to each other. Axial displacement as well as a rotation of the dispensing member 30 equally transfers to the ratchet member 60; and vice versa.

Figure 11:
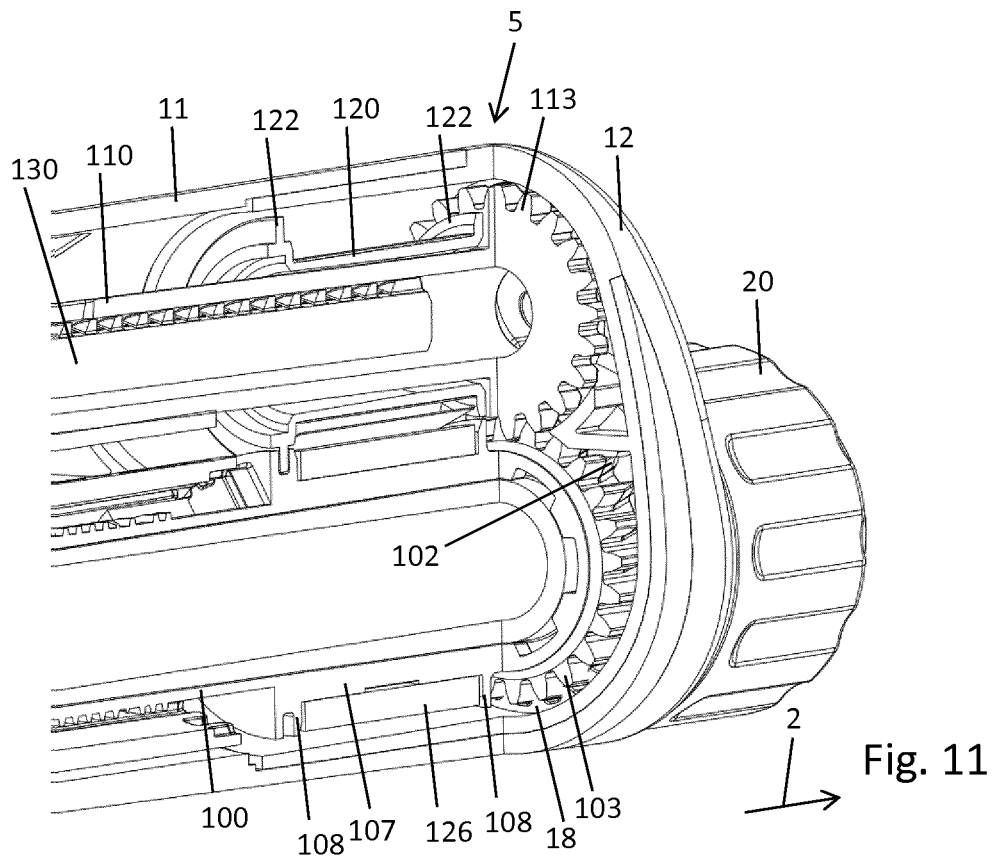
FIG. 11 is a perspective and partially cut view through the proximal end of the device.

There is further provided a drive sleeve 100 having a detent structure 102 at a proximally facing socket portion engaging with a correspondingly-shaped detent structure 18 of the housing 10. The detent structures 18, 102 form a first clutch C1 by way of which the drive sleeve 100 is rotationally locked to the housing 10 when in proximal dose setting position (S). The drive sleeve 100 further comprises a geared section 103 near or at its proximal end as shown in FIGS. 2 and 11. The geared section 103 is in permanent engagement with a correspondingly-shaped geared section 113 of the drive member 110. The geared engagement of drive sleeve 100 and drive member 110 is even invariant to slight axial displacement of the drive sleeve 100 relative to the drive member 110.

Figure 12:
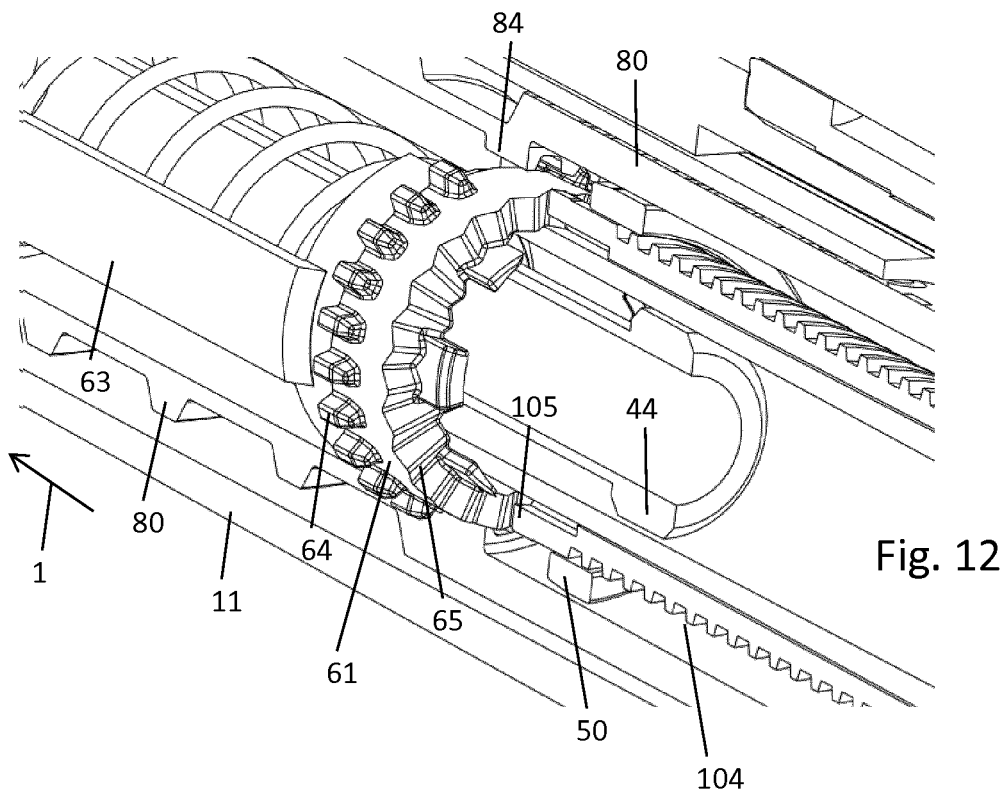
FIG. 12 is another perspective and partially cut view through a middle section of the injection device.
Figure 13:
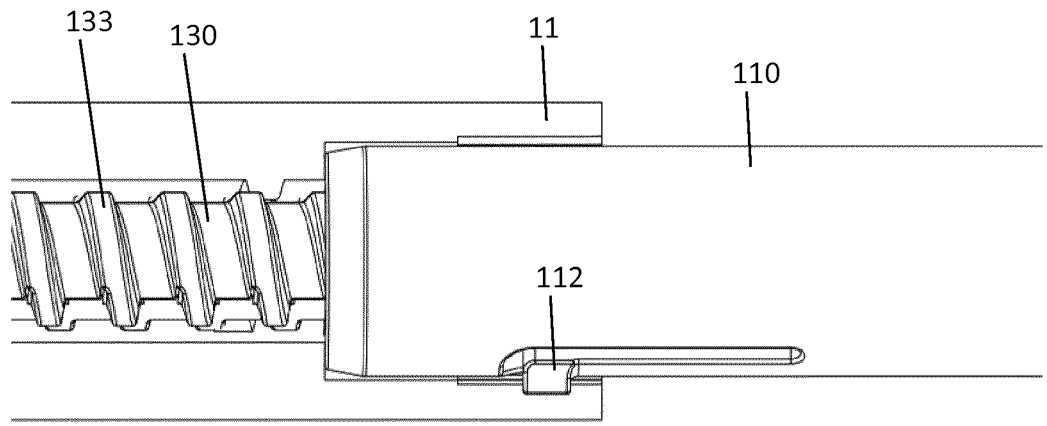
FIG. 13 shows a ratchet engagement between a portion of the main housing and a drive member during dose dispensing.

The drive sleeve 100 is axially intersected by the shaft portion 31 of the dispensing member 30. The drive sleeve 100 further comprises a threaded section 104 near its distal end which is threadedly engaged with a correspondingly threaded last dose limiting member 50 as shown in FIG. 12. The last dose limiting member 50 is furthermore in splined engagement with the inside facing portion of the dose indicator 80 through which the drive sleeve 100 axially extends. During dose setting the dose indicator 80 rotates relative to the rotationally locked drive sleeve 100, thereby inducing a corresponding rotation of the last dose limiter 50, which upon the threaded engagement with the drive sleeve 100 travels in axial direction, e.g. in proximal direction as a dose of increasing size is set.

There are provided mutually corresponding stop features on the outer circumference of the drive sleeve 100 and the last dose limiter 50. When reaching an end of content configuration, in which the dose to be set would exceed the amount of medicament left in the cartridge, the last dose limiter 50 is blocked from rotating further relative to the drive sleeve 100 thereby inhibiting any further dose incrementing rotation of the dose dial 20.

Figure 3:
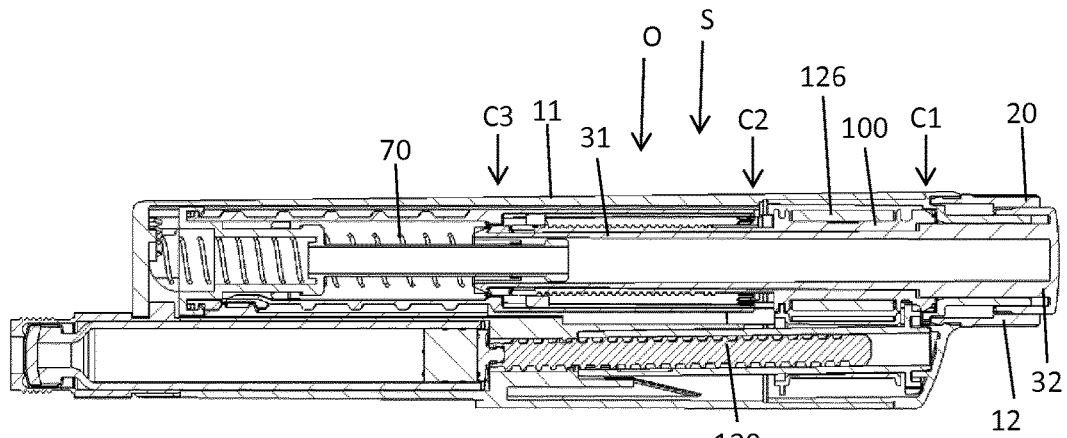
FIG. 3 is a cross-section through the injection device when in dose setting mode.

The ratchet member 60 as it is shown in FIGS. 2 and 12 comprises a proximal rim 61 and a distal rim 62 that are interconnected by at least one bridging portion 63. The proximal rim 61 comprises a toothed profile 64 on its radially outwardly facing circumference to selectively engage with a correspondingly toothed profile 84 of the dose indicator 80. In this way, ratchet member 60 and dose indicator 80 form a torque-proof clutch C3 as indicated in FIG. 3 that is releasable through a distally directed displacement of the ratchet member 60 relative to the main housing 11 and hence relative to the dose indicator 80.

The proximally facing surface of the proximal rim 61 features a ratchet profile 65 that is in engagement with a correspondingly-shaped ratchet profile 105 located at a distal end face of the drive sleeve 100.

In addition, the ratchet member 60 is axially biased by a dispensing spring 70 implemented as a compression spring and extending axially between the proximal rim 61 and a reset member 40 that is axially fixed inside the main housing 11 as long as the drive mechanism 8 is in operating mode O.

In FIGS. 6 and 7 there are shown the sleeve-shaped dose indicator 80 as well as the gauge element 90. The gauge element 90 comprises an elongated and opaque structure with a dose indicating window 91 through which dose indicating numbers of the dose indicator 80 are visible from outside the device. The gauge element 90 is splined to the interior of the main housing 11. It is rotationally locked to the main housing 11 but is free to slide in axial direction relative to the main housing 11. A distal portion of the dose indicator 80 comprises a threaded or helical section 85 that mates and engages a helical section 95 on the inside facing surface portion of the gauge element 90. A rotation of the dose indicator 80 therefore leads to an axial displacement of the gauge element 90. The dose indicator 80 further comprises a zero dose stop 86 as well as a maximum dose stop 87 at axially opposite end sections of the helical section 85. When reaching a minimum or maximum dose configuration the dose indicator 80 with its stops 86, 87 tangentially abuts with correspondingly-shaped stop features of the gauge element 90. In addition the dose indicator 80 comprises a click element 88 to audibly engage with a correspondingly-shaped click element 98 of the gauge element 90 when reaching an initial, hence a zero dose configuration, thereby audibly indicating to a user, that a zero dose configuration, typically at the end of a dispensing procedure has been reached.

Figure 8:
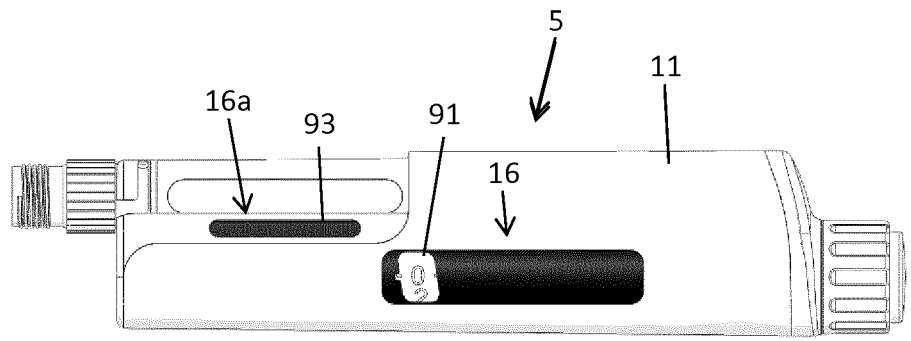
FIG. 8 shows a dose indicating mechanism in a zero dose configuration.
Figure 9:
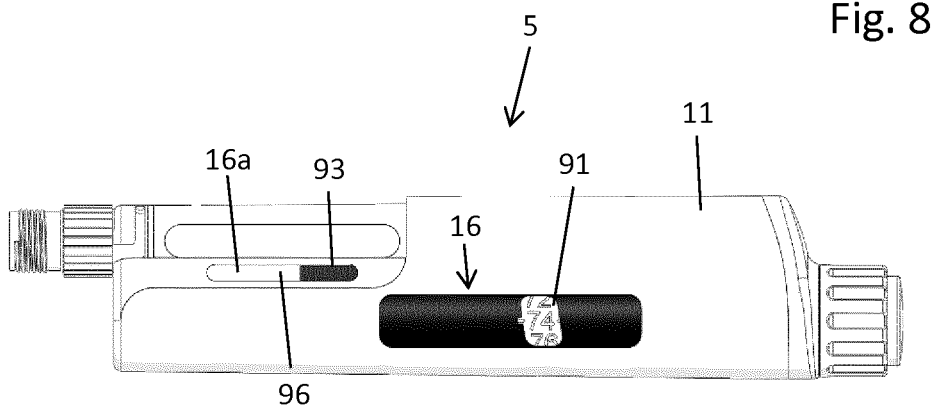
FIG. 9 shows the dose indicating mechanism after a dose of a particular size has been set.

The opaque gauge element 90 is radially sandwiched between the dose indicator 80 and a dose indicating window 16 of the main housing 11 as shown in FIGS. 1, 8 and 9. During a dose setting, in particular during a dose incrementing rotation of the dose indicator 80, the gauge element 90 travels in proximal direction 2, thereby displacing the window 91 to reveal consecutively increasing numbers of the dose indicator 80. At the same time also a distal portion 93 of the gauge element 90 travels in proximal direction 2 which is visible through another window 16a of the main housing 11. The distal portion 93 of the gauge element 90 is of particular use to provide an additional user feedback of the actual dose position of the device. This is of particular use during dose dispensing, namely when the gauge element 90 returns into its distal position as shown in FIG. 8, in which the additional window 16a is completely covered by the gauge element 90. As the gauge element 90 moves in proximal direction during setting of a dose it reveals a further surface underneath as shown in FIG. 9. The axial size of the windows 16, 16a is directly correlated to the maximum size of a dose to be set and dispensed. During the dose dispensing procedure, the progress of dose dispensing is immediately apparent through a comparison of the actual position of the window 91 within the window 16 or by the edge of the distal portion 93 inside the window 16a.

Figure 10:
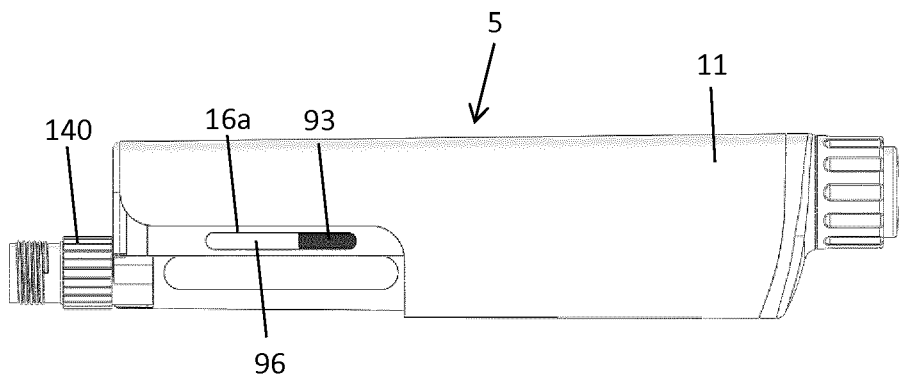
FIG. 10 shows another side view of the device according to FIG. 9.

The axial size of the surface portion 96 as illustrated in FIGS. 9 and 10 is proportional to the dose position of the device and is therefore indicative of the size of the dose currently dialled. The visible surface portion 96 therefore provides an analogue indication or analogue gauge of the size of the dose dialled. As becomes apparent from a comparison of the opposite views of the device according to FIGS. 9 and 10, the additional window 16a may be provided on both sides of the device, which helps to improve overall handling of the device 5 and which helps to improve patient safety.

The analogue gauge provided by the additional window 16a and the distal portion 93 of the gauge element 90 is of particular use during dispensing of a dose. The number digit display provided by the rotating dose indicator 80 may change too quickly for individual dose position markings to be legible. It may be therefore difficult for the user to estimate the rate at which the dose is actually dispensed and the amount of medicament still to be dispensed.

In the following setting of a dose is described. For setting of a dose a user starts to rotate the dose dial 20 in a dose incrementing direction, e.g. clockwise relative to the housing 10. This causes the dispensing member 30 to rotate since dose dial 20 and dispensing member 30 are in permanent rotational interlock. The rotation of the dispensing member 30 equally transfers to a rotation of the ratchet member 60, which due to the ratchet engagement with the ratchet profile 105 of the drive sleeve 100 starts to shuttle axially every time correspondingly-shaped teeth of the ratchet profiles 65, 105 mutually engage.

In this way dialling or setting of a dose is accompanied by an audible click sound as well as by the button portion 32 that shuttles back and forth in axial direction. Since the ratchet member 60 is also rotatably locked to the dose indicator 80 when the drive mechanism 8 is in dose setting mode S also the dose indicator 80 starts to rotate in a dose incrementing direction. In this way a sequence of increasing numbers shows up in the window 91 of the gauge element 90 travelling in proximal direction. During dose setting the drive sleeve 100 is rotatably locked to the main housing 11 through the clutch C1 as illustrated in FIG. 3.

The ratchet member 60 and the dispensing member 30 are biased in proximal direction 2 by means of the dispensing spring 70 extending axially between a radially widened shoulder 46 of the reset member 40 and a distal end face of the ratchet member 60, in particular a distal end face of the ratchet member's 60 proximal rim 61.

In this way, since the drive sleeve 100 is rotationally locked and since the dose indicator 80 rotates in a dose incrementing direction the last dose limiter 50 travels in axial direction as the dose indicator 80 is rotated. In case that the amount of medicament left in the cartridge is smaller than the size of the dose to be set the last dose limiter 50 gets in abutment with a stop element on the outer surface of the drive sleeve 100, thereby preventing any further dose incrementing rotation of the dose indicator 80. The dispensing spring 70 is designed to bias the ratchet member 60 onto the distal end face of the drive sleeve. This axial load acts to maintain the mutually corresponding ratchet profiles 65, 105 in engagement.

A torque required to overhaul the ratchet is governed by the axial load provided by the dispensing spring 70, the ramp angle of the ratchet and the friction coefficient between the mating surfaces and the mean radius of the ratchet profiles 65, 105. As the user rotates the dose dial 20 in a dose incrementing direction, e.g. clockwise, the ratchet member 60 rotates relative to the drive sleeve 100 by consecutive ratchet teeth. Every time a ratchet tooth re-engages into a next detented position an audible click is generated by the mutually engaged ratchet profiles 65, 105. At the same time a tactile feedback is given to the user by the change in torque input required for rotating the dose dial 20.

For increasing a selected dose, the dose dial 20 is simply rotated further, e.g. in clockwise direction. Every time the dose is incremented by a discreet step the re-engagement of the ratchet profiles 65, 105 provides audible and tactile feedback to the user. If the user continues to increase the dose until a maximum dose limit is reached the dose indicator 80 engages with its maximum dose stop 87 with the gauge element 90 thereby preventing any further rotation of the dose indicator 80 and hence any further rotation of the ratchet member 60, the dispensing member 30 and the dose dial 20.

Once a dose of respective size has been set or selected the user is also able to de-select or to decrement the dose. De-selecting of a dose is achieved by the user rotating the dose dial 20 in a dose decrementing direction, e.g. counter-clockwise. The torque to be applied to the dose dial 20 is sufficient to overhaul the ratchet between the ratchet member 60 and the drive sleeve 100 in the dose decrementing direction. When the ratchet is overhauled counter-clockwise also the dose indicator rotates in the opposite direction, thereby consecutively illustrating a sequence of decreasing numbers in the window 91. Also the last dose limiter 50 travels in the opposite axial direction towards its initial position.

Once a dose of required size has been set the drive mechanism 8 may be switched into a dose dispensing mode D by depressing the dispensing member 30 in distal direction 1. When the button portion 32 of the dispensing member 30 is depressed as illustrated for instance in FIG. 5, the ratchet member 60 advances in distal direction 1 against the action of the dispensing spring element 70. The ratchet engagement of the ratchet profiles 65, 105 is disengaged. In addition the clutch C3 between the ratchet member 60 and the dose indicator 80 is disengaged since the ratchet member 60 is displaced axially relative to the dose indicator 80.

Figure 5:
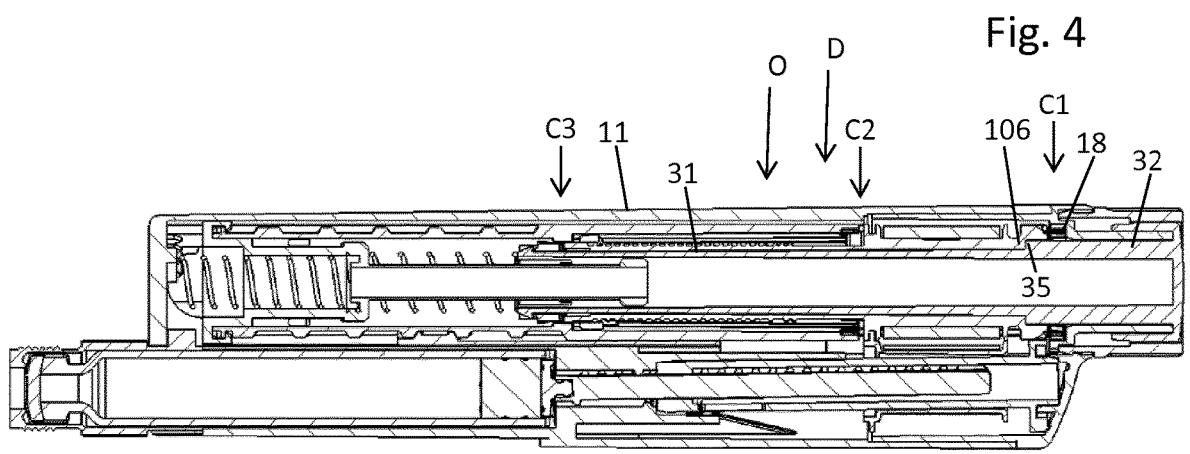
FIG. 5 shows a cross-section through the injection device in dose dispensing mode.

Moreover and due to the axial abutment of dispensing member 30 and drive sleeve 100 also the drive sleeve 100 is displaced in distal direction 1 so that the clutch C1 between drive sleeve 100 and main housing 11 is disengaged or released. Upon axial displacement of the dispensing member 30 a radially widened shoulder portion 35 thereof axially abuts against a correspondingly-shaped shoulder portion 106 of the drive sleeve 100 thereby disengaging the detent structure 102 from the detent structure 18 of the main housing 11 as illustrated in FIG. 5.

Consequently, the drive sleeve 100 is free to rotate under the action of the mainspring 126. With the distally directed displacement of the drive sleeve 100 also a clutch C2 between drive sleeve 100 and dose indicator 80 is engaged.

During dose dispensing the drive sleeve 100 then rotates in a dose decrementing direction, e.g. counter-clockwise. This rotation is equally transferred to a dose decrementing rotation of the dose indicator 80. Hence, during dose dispensing the dose indicator 80 returns into its initial position and the gauge element 90 returns into its initial position as illustrated in FIG. 1. The process of dose dispensing is terminated when the zero dose stop 86 of the dose indicator 80 abuts with a correspondingly-shaped stop of the gauge element 90.

There are further provided mutually engaging click elements 88 and 98 on the dose indicator 80 and the gauge element 90 that audibly engage when the zero dose configuration has been reached. The click element 88 may comprise a flexible arm which may be radially outwardly biased by the axial and distal displacement of the ratchet member 60, in particular of its distal rim 62. In this way, the click element 88 of the dose indicator 80 may be radially outwardly biased by the ratchet member 60 when switched into the dose dispensing mode D. In this way, a rather loud and distinct click noise is generated directly indicating to a user, that dose dispensing has terminated.

The drive sleeve 100 is permanently rotatably engaged via the geared section 103, 113 with the drive member 110. As already explained a rotation of the drive member 110 in dose decrementing direction leads to a distally directed displacement of the piston rod 130. In addition the drive member 110 comprises a radially outwardly protruding click element 112 engaging with a correspondingly-shaped toothed profile on the interior surface of the main housing 11. In this way, delivery of a dose and hence a rotation of the drive member 110 is also accompanied by an audible click sound with each dose increment delivered.

Delivery and dispensing of a dose continues as described above while the user keeps the dispensing member 30 in a depressed position. If the user releases the dispensing member 30, the dispensing member 30 immediately returns into its initial and proximal dose setting position under the effect of the dispensing spring 70. Consequently, also the ratchet member 60 and the drive sleeve 100 return into their dose setting positions, thereby engaging the clutches C1, C3 but releasing the clutch C2.

During dose dispensing the dose indicator 80 and the drive sleeve 100 rotate together. Since there is no relative rotation between the drive sleeve 100 and the dose indicator 80 the last dose limiter 50 remains in its axial position relative to the drive sleeve 100 and the dose indicator 80.

Once the dispensing procedure is stopped by the dose indicator 80 getting in abutment with the gauge element 90 the mainspring-driven rotation of the drive sleeve 100 stops. When the user releases the dispensing member 30, in particular its button portion 32 the drive sleeve 100 will re-engage with the main housing 11 and the ratchet member 60 will re-engage with the dose indicator 80.

Figure 14:
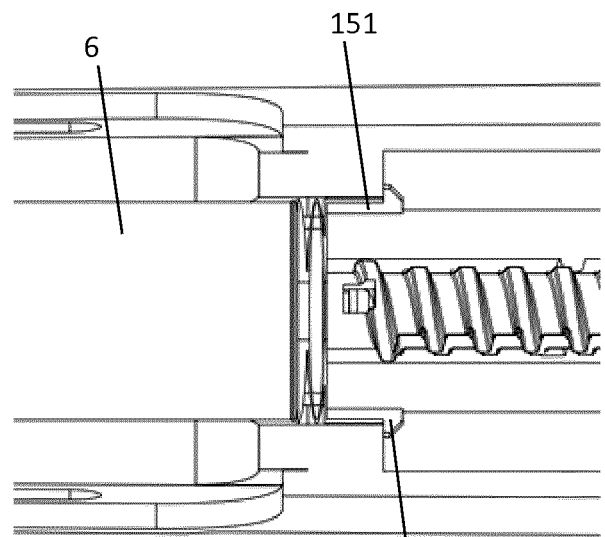
FIG. 14 shows the arrangement of a bias spring at a proximal end of the cartridge.
Figure 15:
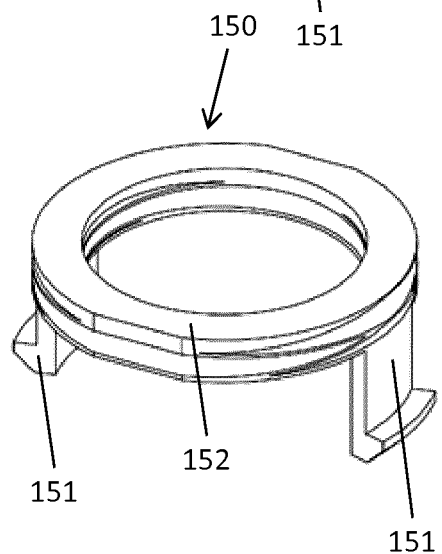
FIG. 15 shows an isolated and perspective view of the bias spring.

As it is further illustrated in FIGS. 14 and 15 the injection device 5 comprises a bias spring 150 arranged in axial abutment with the proximal end of the cartridge 6 as shown in FIG. 14. The bias spring 150 as shown in FIG. 15 comprises two snap features 151 by way of which the bias spring 150 is axially fixable to the main housing 11. The bias spring 150 further comprises an annular rim 152 that gets in direct axial abutment with a proximal end of the cartridge 6. It is actually the rim 152 that forms or comprises a compression spring element acting in axial direction.

In this way the bias spring 150 exerts a distally directed bias onto the cartridge 6 which helps to reduce or to remove any detrimental effect arising from geometry tolerances of the cartridge length. Moreover, by means of the bias spring 150 a cartridge removal may be facilitated. Upon releasing and removing of the cartridge holder 140 the cartridge 6 may be axially displaced in distal direction 1 under the effect of the bias spring 150.

The rim 152 of the bias spring 150 comprises an inner diameter that is larger than the radial extent of a bearing 132 rotatably attached to the distal end of the piston rod 130. The bearing 132 acts as a pressure piece and gets in direct axial abutment with the proximal thrust receiving surface of the piston 7 of the cartridge 6. The bearing 132 is free to rotate with regard to the first axis on the distal end of the piston rod 130. In this way, a rotation of the piston rod 130 during dose dispensing does not transfer to the piston 7 of the cartridge 6.

The mainspring 126 providing a mechanical energy storage and providing sufficient torque to expel the amount of medicament contained in the cartridge 6 comprises an elongated strip of material that has been rolled or coiled such that its natural state is to form a tightly wound spiral with a comparatively small inner diameter. One end of the elongated material strip is engaged and connected to the drive sleeve 100. The drive sleeve 100 comprises a respective coil portion 107 axially constrained by flange portions 108 as shown in FIG. 11 that allows for a smooth and well-defined coiling of the elongated material strip of the mainspring 126.

There is further provided a storage spool 120 radially adjacent to the coil portion 107 of the drive sleeve 100. The storage spool 120 is axially intersected by the drive member 110 and is free to rotate on the outer circumference of the drive member 110. Also the storage spool comprises a distal and a proximal flange portion 122 in order to axially constrain the mainspring 126. The mainspring 126, hence the elongated strip of material, tends to coil itself onto the storage spool 120. Since one end of the mainspring 126 is anchored to the drive sleeve 100 the mainspring 126 is chargeable by rotating the drive sleeve 100 in a dose incrementing direction thereby coiling up the elongated strip of material onto the coil portion 107 of the drive sleeve 100.

Once charged the majority of material of the mainspring 126 is wrapped around the drive sleeve 100. During consecutive dispense procedures the elongated strip of material transfers back to the storage spool 120 thereby inducing a number of dose decrementing rotations of the drive sleeve 100.

Figure 16:
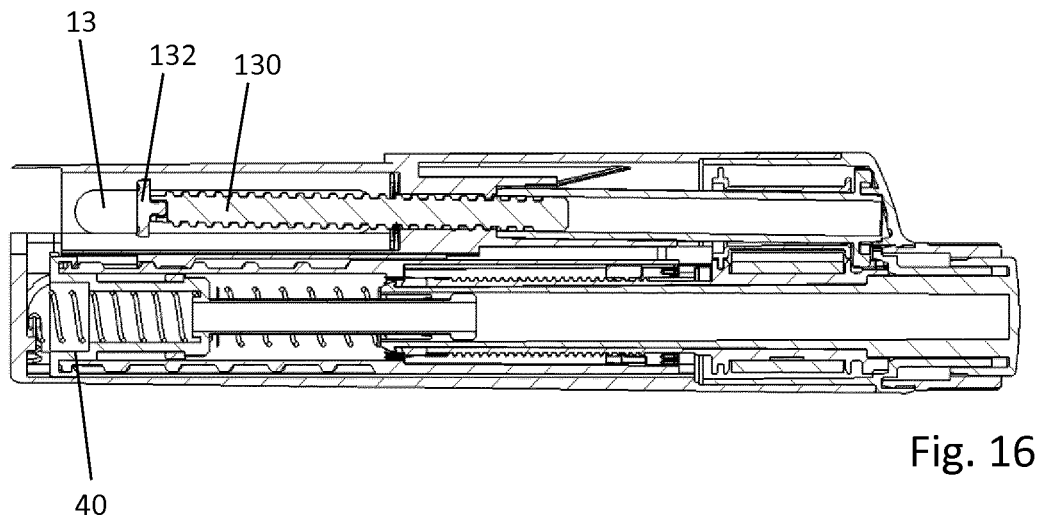
FIG. 16 shows the injection device just after removal of a cartridge holder.

In the following the reset functionality of the drive mechanism 8 is described. To reset the mechanism and to replace an empty cartridge 6 by a new one the cartridge holder 140 is disconnected from the main housing 11, typically by way of a twisting motion. Such a configuration is shown in FIG. 16, where the cartridge holder 140 and the cartridge 6 have already been removed.

Figure 22:
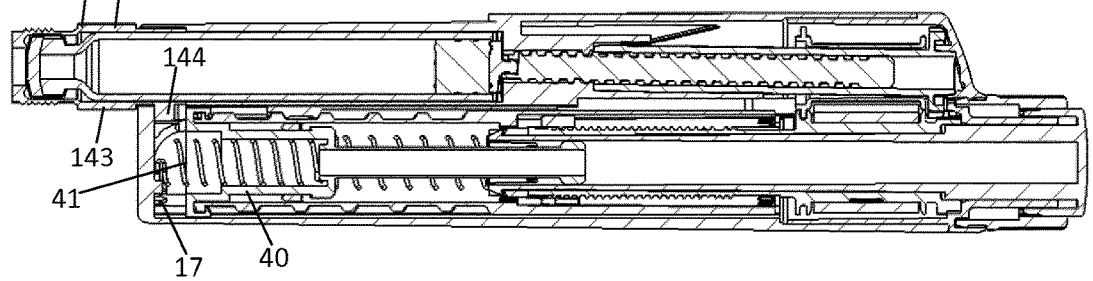
FIG. 22 shows the device according to FIG. 21 with the cartridge holder connected thereto.
Figures 23A, 23B, 23C:
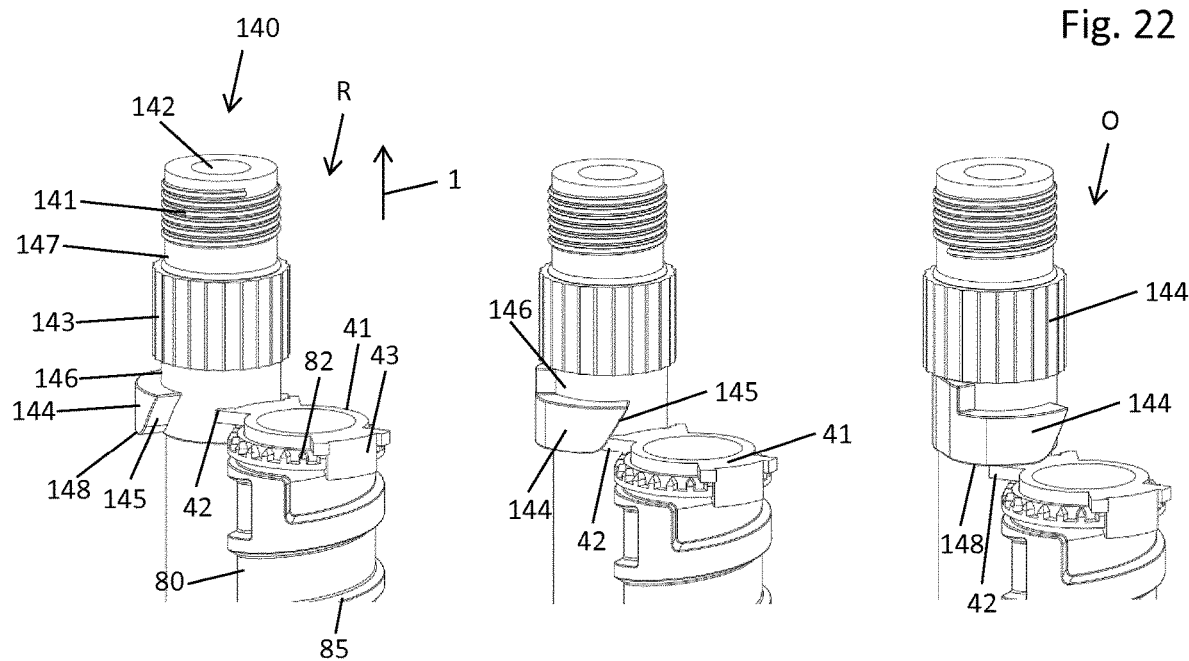
FIG. 23a shows the cartridge holder in an unlocked configuration.
FIG. 23b shows the cartridge holder when twisted towards a locking configuration thereby engaging a distal edge of the reset member with its cam portion and FIG. 23c shows the cartridge holder when in locked configuration, thereby axially proximally displacing the reset member into the operating position.

The cartridge holder 140 as shown in FIGS. 23a-23c comprises a somewhat cylindrical shape with a sidewall portion 147 from which a lock member 144 radially outwardly protrudes. This lock member 144 is provided with a cam portion 145 at a tangential end. A comparison of FIGS. 21 and 22 reveals that the lock member 144 enters a recess 15 adjacent to a distal front face 14 of the main housing 11. As shown in FIG. 22 the lock member 144 and hence the cam portion 145 is axially sandwiched between a distal end 41 of a reset member 40 and the proximally facing inside of the front face 14.

The reset member 40 is located radially adjacent to the cartridge 6 and also radially adjacent to a receptacle 13 of the main housing 11 that serves to accommodate a major proximal portion of the cartridge 6. By means of twisting the cartridge holder 140 with regard to the first axis 3 and relative to the main housing 11 distal displacement of the reset member 40 is no longer blocked by the lock member 144 and the reset member 40 is allowed to advance in distal direction 1 under the combined action of the dispensing spring 70 and the reset spring 76.

The reset member comprises a tubular-shaped receptacle that is open towards the distal direction and which accommodates the reset spring 76. One end of the reset spring is attached to a proximally located bottom portion of the receptacle 47 while the oppositely located end of the reset spring 76 is fastened to the front face 14 of the main housing 11. In the present embodiment the reset spring 76 is configured as an extension spring and serves to drag the reset member 40 in distal direction and to bring the reset member 40 in axial abutment with the front face 14 of the main housing 11.

Figure 17A:
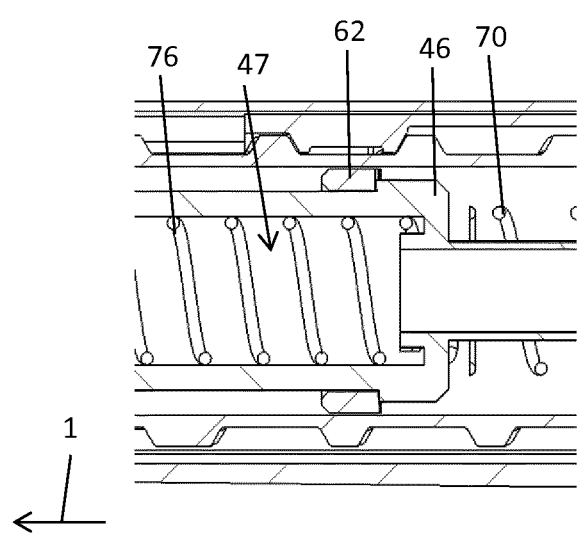
FIG. 17a is an enlarged view of a distal portion of the cross-section according to FIG. 16.

The axial displacement of the reset member 40 is apparent from a comparison of FIGS. 16 and 17a. Near its distal end the reset member 40 comprises radially outwardly and proximally extending clips 43 that engage with a circumferential groove 89 of the dose indicator 80. In this way, the reset member 40 and the dose indicator 80 are axially engaged. At least one of the clips 43 extending radially outwardly from the tubular-shaped receptacle 47 of the reset member 40 may be splined to the housing and may be axially guided in a correspondingly-shaped groove 19 of the main housing 11 as shown in FIG. 19a.

In this way the reset member 40 is rotationally locked to the main housing 11. The dose indicator 80 further comprises a detent structure 82, e.g. in form of a crown wheel at its distal front face. This detent structure 82 is configured to engage with a correspondingly-shaped detent structure 17 located at an inside portion of the front face 14 of the main housing 11. As the reset member 40 advances in distal direction 1 the dose indicator 80 experiences a corresponding or equal axial displacement bringing the detent structure 82 and the detent structure 17 in mutual engagement. In this way the dose indicator 80 is rotationally locked to the main housing 11 when the injection device 5 is switched into the reset mode. Hence, a clutch C5 is engaged as indicated in FIG. 18. As a result of the axial displacement of the dose indicator 80, the window 91 of the gauge element 90 advances in distal direction so that it may be no longer visible in the window 16 of the main housing 11, thereby indicating to the user, that a reset procedure is actually in progress.

The reset member 40 is also selectively axially engageable with the ratchet member 60, in particular with the distal rim 62 of the ratchet member 60. The reset member 40 comprises a distally facing ratchet profile 48 on its outer circumference. The reset member 40 further comprises a receptacle 47 which is open in distal direction and which serves to receive a reset spring 76 as shown in detail in FIG. 4. The distally advancing reset member 40 then axially engages with a correspondingly-shaped ratchet profile 68 of the ratchet member 60, in particular of the distal rim 62 of the ratchet member 60. The ratchet profile 68 faces in proximal direction so as to engage the distally facing corresponding ratchet profile 48 of the reset member 40.

Once a mutual axial abutment has been reached between reset member 40 and ratchet member 60 as shown for instance in FIG. 17a, a further distally directed displacement of the reset member 40 under the combined action of the dispensing spring 70 and the reset spring 76 leads to a further axial and distal displacement of the ratchet member 60. Since the ratchet member 60 is axially locked to the dispensing member 30 also the dispensing member 30 is moved in distal direction 1 as becomes apparent from a comparison of FIGS. 16 and 18. The button portion 32 of the dispensing member 30 is retracted axially into the main housing 11 and radially flushes with the proximal end of the dose dial 20.

The distally directed displacement of the dispensing member 30 transfers to a respective distally directed displacement of the drive sleeve 100 so that the clutch C1 disengages without engaging of the clutch C2. Hence, the distally directed displacement of reset member 40, ratchet member 60, dispensing member 30 and drive sleeve 100 is such that the drive sleeve 100 is rotationally disengaged from the main housing 11 but does not engage with the dose indicator 80. A re-engagement of drive sleeve 100 and dose indicator 80 is effectively prevented, since the dose indicator is also moved in distal direction due to its axial engagement with the reset member 40.

Figure 4:
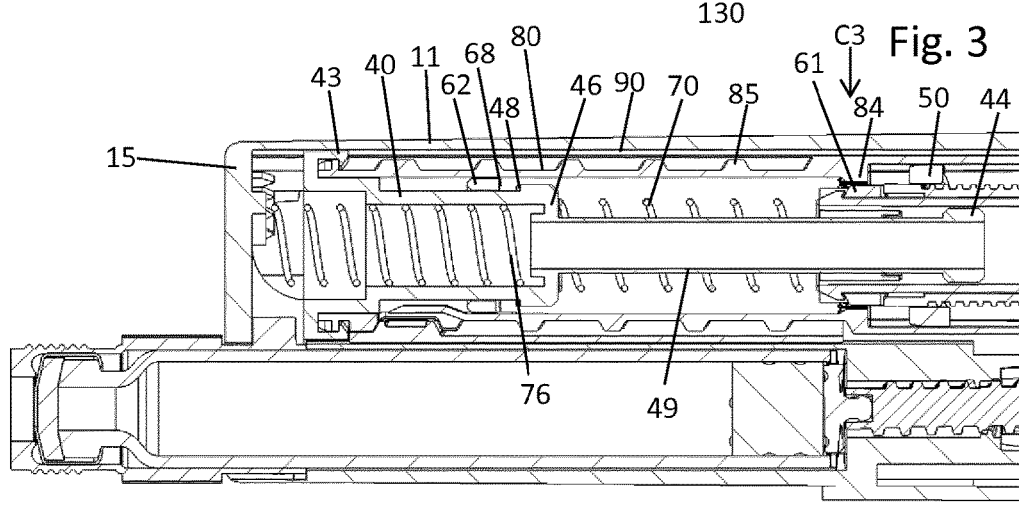
FIG. 4 is an enlarged view of a portion of the cross-section according to FIG. 3.

In contrast to the dose dispensing action the dose indicator 80 also travels in distal direction. The distal displacement of the dose indicator in distal direction is even larger than the distal displacement of the ratchet member 60 in distal direction. This is attained through the fact that in operating position 8 as illustrated in FIG. 4 there exists an at least small axial gap between the mutually corresponding ratchet profiles 48, 68 of reset member 40 and ratchet member 60. When reaching the reset position the dose indicator 80 has advanced in distal direction in comparison to the ratchet member 60, thereby disengaging the clutch C3 so that the ratchet member 60 and the dispensing member 30 are free to rotate relative to the dose indicator 80.

Figure 17B:
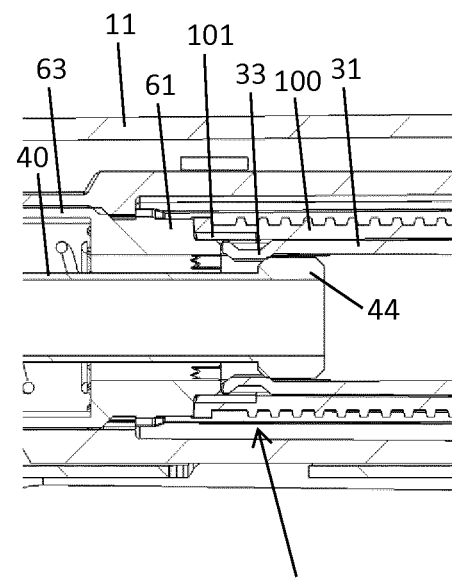
FIG. 17b is an enlarged view of a middle section of the device according to FIG. 16.

Before the clutch C1 is disengaged a torque-proof clutch C4 as shown in FIG. 17b between dispensing member 30 and drive sleeve 100 is engaged. In this way the dispensing member 30 and hence the dose dial 20 is rotatably locked to the drive sleeve 100. This is not only to prevent an uncontrolled release of mechanical energy from the mainspring 126 upon releasing of the clutch C1 but also to provide a torque-proof engagement between the dose dial 20 and the drive sleeve 100. Activation of the clutch C4 is obtained by means of a head portion 44 located at a distal end of the reset member 40.

The head portion 44 is located inside the hollow shaft of the dispensing member 30. The head portion 44 is furthermore arranged at a proximal end of the reset member. The reset member 40 comprises a tubular shaped receptacle 47 at its distal end and further has a longitudinal shaft portion 49 extending in proximal direction 2. At the proximal end of the shaft portion 49 the head portion 44 is located protruding radially outwardly from the shaft portion and having at least bevelled or conical surface facing in distal direction 1. The shoulder portion 46 forms a transition between the distal receptacle 47 and the proximal shaft portion 49. The shaft portion 49 further supports and axially intersects the dispensing spring 70.

Axial displacement of the reset member 40 in distal direction 1 brings the radially widened head 44 in axial and radial abutment with resilient latch elements 33 that extend radially inwardly from an inside facing sidewall portion of the dispensing member's 30 shaft portion 31. Due to the axial distal displacement of the reset member 40 and hence of its head portion 44 relative to the dispensing member 30 at the beginning of the reset member's distally directed displacement the latch elements 33 are urged radially outwardly to engage with correspondingly-shaped recesses 101 provided on the inside facing portion of the hollow drive sleeve 100. In this way a torque-proof and rotational engagement of dispensing member 30 and drive sleeve 100 is obtained.

In this reset position R as shown in FIG. 18 the dose dial 20 is rotatable in dose incrementing direction, e.g. clockwise. This rotation transfers to the dispensing member 30 and to the ratchet member 60. The ratchet engagement between the ratchet member 60 and the reset member 40 is overhauled when sufficient torque is applied to the dose dial 20. Clockwise and anti-clockwise ramp angles of the ratchet profiles 48, 68 of the reset member 40 and the ratchet member 60 respectively are designed such that the user may rotate the dose dial 20 and hence the dispensing member 30 and the drive sleeve 100 in dose incrementing direction so as to charge the mainspring 126 but that stored spring energy does not cause the drive sleeve 100 to rotate in the opposite direction, hence in dose decrementing direction. Hence, for resetting the dose dial 20 has to be twisted and rotated in the same direction as for increasing a dose in dose setting mode.

Since the dose indicator 80 is rotationally locked to the main housing 11 and since the drive sleeve 100 rotates in dose decrementing direction the last dose limiter 50 returns into its initial zero dose position. Rotation of the drive sleeve 100 during the reset operating is equally transferred to the drive member 110 thereby inducing a proximally directed retraction and displacement of the piston rod 130. The outer thread 133 of the piston rod is threadedly engaged with a threaded web or flange portion 9 of the main housing 11 as for instance shown in FIG. 20.

Figure 21:
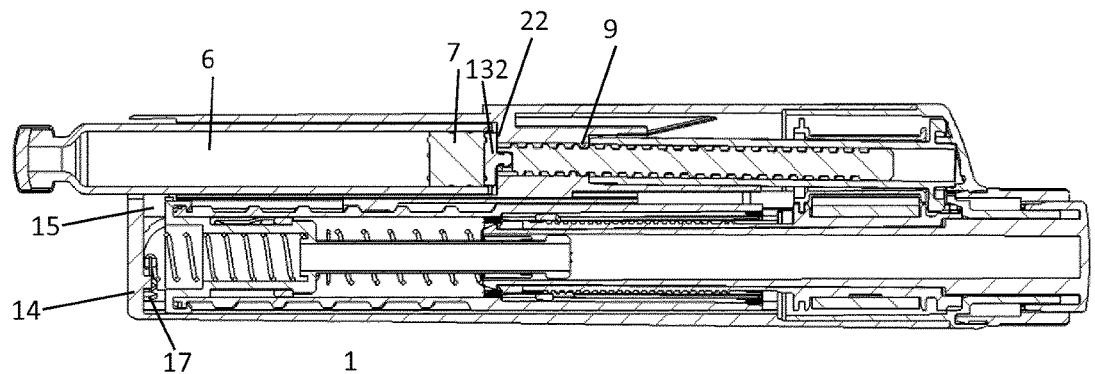
FIG. 21 is illustrative of the device after replacement of the cartridge.

The reset operation terminates when the bearing 132 axially abuts with a stop face 22 of the main housing 11 as shown in FIG. 21.

In such a configuration a new cartridge 6 can be fitted into the receptacle 13 so that a proximal thrust receiving surface of the cartridge's piston 7 axially abuts with a distal thrust exerting surface of the bearing 132. In addition the cartridge 6 can be axially inserted into the receptacle 13 against the action of the bias spring 150. Once the cartridge 6 has been assembled inside the main housing 11 the cartridge holder 140 can be placed over the distal end of the cartridge 6 and can be locked to the main housing 11 as shown in FIGS. 22-23c.

The cartridge holder 140 arranged along the first axis 3 is fitted over the distal end of the cartridge 6 so that a radially widened rim of its gripping surface 143 axially abuts in proximal direction 2 against the outside facing portion of the front face 14 of the main housing 11. It is then due to a twisting motion of the cartridge holder 140 that the lock member 144 radially outwardly protruding from a substantially tubular-shaped sidewall portion 147 enters a recess 15 thereby engaging a tilted cam portion 145 with a distal edge 42 of the reset member 40 as shown in FIG. 23b. A further twisting motion of the cartridge holder 140 leads to the configuration as shown in FIG. 23c. The distal edge 42 of the reset member 40 travels along the tilted cam portion 145 until a proximally facing surface of the lock member 144 axially abuts with the distally facing front face 41 of the reset member 40.

In this way, the twisting motion of the cartridge holder 140 during re-attachment of the cartridge holder 140 to the main housing 11 induces a proximally directed displacement of the reset member 40 against the combined action of the dispensing spring 70 and the reset spring 76 thereby switching the drive mechanism 8 from the reset mode R into the operating mode O.

As indicated in FIG. 23b the lock member 144 is arranged at a well-defined axial distance to the radially thickened gripping surface 143. In other words, there is provided an axial gap 146 between the lock member 144 and the gripping surface 143 extending in tangential direction that matches with the axial thickness of the front face 14 of the main housing 11. Upon twisting of the cartridge holder 140 into a locked configuration as shown in FIGS. 22 and 23c the cartridge holder 140 axially engages with the main housing 11, in particular with its front face 14. When the front face 14 enters the axial and tangential slit 146 the cartridge holder 140 is automatically axially fixed and locked to the main housing 11.

By means of the lock member 144 radially outwardly protruding from the sidewall portion 146 of the cartridge holder 140 a twisting motion of the cartridge holder 140 is transferable to an axial displacement of the reset member 40 which is located radially offset to the cartridge holder 140 and which is arranged in a radially non-overlapping configuration to the cartridge holder 140. A proximally facing abutment surface 148 of the lock member 144 engages and abuts with the distal end face 41 of the reset member 40.

As the reset member 40 is displaced into its proximal operating position O the drive sleeve 100 returns into its operating position, hence into its dose setting position in which the clutch C1 is engaged. Thereafter, upon a further proximally directed displacement of the reset member 40 the clutch C4 disengages, the dose indicator 80 is rotationally released from the main housing 11 and the ratchet member 60 re-engages with the drive sleeve 100 via the ratchet engagement and further rotationally locks to the dose indicator 80.

The dispensing spring 70 ensures that the ratchet member 60, the dispensing member 30 and the drive sleeve 100 are displaced axially in proximal direction with regard to the reset member 40.

LIST OF REFERENCE NUMERALS 1 distal direction
2 proximal direction
3 axis
4 axis
5 injection device
6 cartridge
7 piston
8 drive mechanism
9 flange
10 housing
11 main housing
12 proximal housing portion
12a socket portion
13 receptacle
14 front face
15 recess
16 window
16a window
17 detent structure
18 detent structure
19 groove
20 dose dial
21 clip member
22 stop face
30 dispensing member
31 shaft portion
32 button portion
33 latch element
34 snap member
35 shoulder portion
40 reset member
41 distal end
42 distal edge
43 clip
44 head
46 shoulder
47 receptacle
48 ratchet profile
49 shaft portion
50 last dose limiter
60 ratchet member
61 proximal rim
62 distal rim
63 bridge portion
64 toothed profile
65 ratchet profile
68 ratchet profile
70 dispensing spring
76 reset spring
80 dose indicator
81 distal end
82 detent structure
84 toothed profile
85 helical section
86 stop
87 stop
88 click element
89 groove
90 gauge element
91 window
93 distal portion
95 helical section
96 surface portion
98 click element
100 drive sleeve
101 recess
102 detent structure
103 geared section
104 threaded section 105 ratchet profile
106 shoulder portion
107 coil portion
108 flange portion
110 drive member
112 click element
113 geared section
120 storage spool
122 flange portion
126 mainspring
130 piston rod
132 bearing
133 outer thread
140 cartridge holder
141 threaded socket
142 through opening
143 gripping surface
144 lock member
145 cam portion
146 gap
147 sidewall portion
148 abutment face
150 bias spring
151 snap feature
152 rim

The invention claimed is:

1. An injection device for setting and dispensing of a dose of a medicament, the injection device comprising:
   an elongate housing to accommodate a cartridge filled with the medicament;
   a piston rod arranged inside the housing and extending longitudinally along a first axis to operably engage with a piston of the cartridge;
   a reset member axially displaceable inside the housing between a proximal operating position and a distal reset position along a second axis radially offset from the first axis to switch the injection device between a reset mode and an operating mode; and
   a cartridge holder releasably attachable to a distal end of the housing on the first axis to accommodate a distal end of the cartridge, wherein the cartridge holder comprises a sidewall portion with a radially outwardly protruding lock member to axially engage with the reset member located radially adjacent the cartridge holder,
   wherein a cam portion of the lock member is configured to tangentially engage the reset member such that the reset member is displaced proximally toward the proximal operating position when the cartridge holder is twisted relative to the housing about the first axis.

2. The injection device according to claim 1, wherein the reset member is displaceable distally, by at least one spring element, into the distal reset position.

3. The injection device according to claim 1, wherein a distal end of the reset member axially abuts an inside of a distally located front face of the housing when reaching the distal reset position.

4. The injection device according to claim 1, wherein the cam portion of the lock member is configured to tangentially engage a distal edge of the reset member such that the reset member is displaced proximally toward the proximal operating position when the cartridge holder is twisted relative to the housing about the first axis.

5. The injection device according to claim 1, wherein the lock member is axially between the reset member and an inside of a distally located front face of the housing when the reset member is in the proximal operating position.

6. The injection device according to claim 1, wherein the reset member is axially engaged with a dose indicator rotationally supported on the second axis and having numbers or symbols, consecutive portions of the numbers or symbols being visible through a window of the housing when the dose indicator is subject to a dose incrementing rotation during dose setting or when the dose indicator is subject to a dose decrementing rotation during dose dispensing.

7. The injection device according to claim 6, wherein the dose indicator comprises a detent structure at a distal end of the dose indicator to engage with a corresponding detent structure of the housing when the reset member reaches the distal reset position.

8. The injection device according to claim 1, further comprising a drive sleeve permanently rotationally coupled to the piston rod and rotationally biased by a spring, the drive sleeve being configured to be rotationally locked to the housing in a dose setting mode and rotationally released from the housing in a dose dispensing mode.

9. The injection device according to claim 1, further comprising:
   a dispensing member aligned along the second axis with a distal shaft portion and a proximal button portion,
   wherein the dispensing member is displaceable distally against an action of a dispensing spring element to switch from a dose setting mode to a dose dispensing mode.

10. The injection device according to claim 9, further comprising a ratchet member permanently axially and rotationally locked to the dispensing member.

11. The injection device according to claim 10, wherein the ratchet member is alternately engaged with a drive sleeve in the dose setting mode and with the reset member in the reset mode.

12. The injection device according to claim 10, wherein the ratchet member is configured to be rotationally locked to a dose indicator in the dose setting mode and to be rotationally released from the dose indicator in the dose dispensing mode.

13. The injection device according to claim 10, wherein the reset member is configured to axially engage with the ratchet member when approaching the distal reset position, thereby distally displacing the ratchet member into a reset position in which the ratchet member is disengaged from a drive sleeve.

14. The injection device according to claim 9, wherein the dispensing member is in axial abutment with a drive sleeve to displace the drive sleeve into a distal reset position in which the drive sleeve is rotatably released from the housing and from a dose indicator.

15. The injection device according to claim 9, wherein:
   the dispensing member axially intersects a hollow drive sleeve of the injection device,
   a proximal head of the reset member located inside the dispensing member is configured to engage with at least one latch member of the dispensing member when the reset member is being distally displaced toward the reset position, thereby activating a torque-proof clutch between a drive sleeve and the dispensing member.

16. A reset mechanism for an injection device, the reset mechanism comprising:
   a reset member axially displaceable inside a housing of the injection device between a proximal operating position and a distal reset position along a second axis radially offset from a first axis defined by the housing of the injection device to switch the injection device between a reset mode and an operating mode; and a cartridge holder releasably attachable to the housing of the injection device, the cartridge holder comprising a lock member radially outwardly protruding, the lock member configured to axially engage with the reset member, wherein a cam portion of the lock member is configured to tangentially engage the reset member such that the reset member is displaced proximally toward the proximal operating position when the cartridge holder is twisted relative to the housing about the first axis.

17. The reset mechanism according to claim 16, wherein the cam portion of the lock member is configured to tangentially engage a distal edge of the reset member such that the reset member is displaced proximally toward the proximal operating position when the cartridge holder is twisted relative to the housing about the first axis.

18. The reset mechanism according to claim 16, wherein the lock member is axially between the reset member and an inside of a distally located front face of the housing when the reset member is in the proximal operating position.

19. A method of operating an injection device, the method comprising:

disconnecting a cartridge holder of the injection device from a distal end of a housing of the injection device on a first axis of the housing, thereby causing a reset member of the injection device to move axially from an operating position to a reset position along a second axis of the housing radially offset from the first axis, wherein disconnecting the cartridge holder from the distal end of the housing comprises twisting the cartridge holder relative to the housing about the first axis to cause the reset member to move along the second axis to the reset position;

loading a cartridge into the housing along the first axis of the housing; and connecting the cartridge holder to the distal end of the housing on the first axis of the housing, thereby causing the reset member to move along the second axis of the housing from the reset position to the operating position, wherein connecting the cartridge holder to the distal end of the housing comprises twisting the cartridge holder relative to the housing about the first axis to cause the reset member to move along the second axis to the operating position.

* * * * *